(12) United States Patent
Todd

(10) Patent No.: US 7,753,526 B2
(45) Date of Patent: Jul. 13, 2010

(54) FREQUENCY DOUBLING FIXATION STIMULI FOR VISUAL FIELD TESTING AND THERAPY

(75) Inventor: David P. Todd, Boynton Beach, FL (US)

(73) Assignee: NovaVision, Inc., Boca Raton, FL (US)

( * ) Notice: Subject to any disclaimer, the term of this patent is extended or adjusted under 35 U.S.C. 154(b) by 159 days.

(21) Appl. No.: 11/881,142

(22) Filed: Jul. 25, 2007

(65) Prior Publication Data

US 2008/0024724 A1    Jan. 31, 2008

Related U.S. Application Data

(60) Provisional application No. 60/833,199, filed on Jul. 25, 2006, provisional application No. 60/867,499, filed on Nov. 28, 2006.

(51) Int. Cl.
*A61B 3/02* (2006.01)
*A61B 3/10* (2006.01)

(52) U.S. Cl. .................... 351/237; 351/211; 351/224

(58) Field of Classification Search .......... 351/200–246
See application file for complete search history.

(56) References Cited

U.S. PATENT DOCUMENTS

| | | | |
|---|---|---|---|
| 1,463,847 A | 8/1923 | Shilling | |
| 2,213,484 A | 9/1940 | Briggs | 128/76.5 |
| 3,883,234 A | 5/1975 | Lynn et al. | 351/23 |
| 4,260,227 A | 4/1981 | Munnerlyn et al. | 351/24 |
| 4,408,846 A | 10/1983 | Balliet | 351/203 |
| 4,421,392 A * | 12/1983 | Pitts Crick et al. | 351/224 |
| 4,429,961 A | 2/1984 | Sheingorn | 351/226 |
| 4,533,221 A | 8/1985 | Trachtman | 351/203 |
| 4,660,945 A | 4/1987 | Trachtman | 351/203 |
| 4,679,920 A | 7/1987 | Takashi et al. | 351/226 |
| 4,971,434 A | 11/1990 | Ball | 351/224 |
| 4,995,717 A * | 2/1991 | Damato | 351/224 |
| 5,035,500 A * | 7/1991 | Rorabaugh et al. | 351/226 |
| 5,050,982 A | 9/1991 | Meissner | 351/203 |
| 5,088,810 A | 2/1992 | Galanter et al. | 351/203 |
| 5,139,323 A | 8/1992 | Schillo | 351/45 |
| 5,147,284 A | 9/1992 | Fedorov et al. | 600/9 |

(Continued)

FOREIGN PATENT DOCUMENTS

DE    9305147    4/1994

(Continued)

OTHER PUBLICATIONS

Portable Tech/Emory Device Checks for Concussions, Apr. 26, 2005.

(Continued)

*Primary Examiner*—Mohammed Hasan
(74) *Attorney, Agent, or Firm*—Sunstein Kann Murphy & Timbers LLP

(57) ABSTRACT

Alteration of a fixation or peripheral stimulus displayed on a computer-driven display allows a human subject to maintain extended visual fixation upon the resulting dynamic stimulus. The fixation is presented upon the display and the stimulus is altered to allow resensitization of the subject's retina, thereby allowing prolonged visual fixation upon the resulting dynamic target. A dynamic stimulus may utilize a frequency doubling illusion.

7 Claims, 22 Drawing Sheets

U.S. PATENT DOCUMENTS

| | | | |
|---|---|---|---|
| 5,191,367 A | 3/1993 | Salibello et al. | 351/243 |
| 5,206,671 A | 4/1993 | Eydelman et al. | 351/203 |
| 5,241,332 A | 8/1993 | Farrell | 351/246 |
| 5,305,027 A | 4/1994 | Patterson | 351/44 |
| 5,321,445 A | 6/1994 | Fossetti | 351/203 |
| 5,325,136 A | 6/1994 | Salibello et al. | 351/243 |
| 5,363,154 A | 11/1994 | Galanter et al. | 351/203 |
| 5,455,643 A | 10/1995 | Ki-Ho | 351/203 |
| 5,534,953 A | 7/1996 | Schmielau | 351/203 |
| 5,539,481 A | 7/1996 | Vax | 351/203 |
| 5,539,482 A | 7/1996 | James et al. | 351/246 |
| 5,550,602 A | 8/1996 | Braeuning | 351/243 |
| 5,565,949 A | 10/1996 | Kasha, Jr. | 351/243 |
| 5,883,692 A | 3/1999 | Agonis et al. | 351/224 |
| 5,886,770 A | 3/1999 | Damato | 351/237 |
| 5,912,723 A | 6/1999 | Maddess | 351/246 |
| 5,946,075 A | 8/1999 | Horn | 351/246 |
| 5,991,085 A | 11/1999 | Rallison et al. | 359/630 |
| 6,061,593 A | 5/2000 | Fischell et al. | 600/544 |
| 6,062,687 A | 5/2000 | Lofgren-Nisser | 351/46 |
| 6,286,960 B1 | 9/2001 | Tomita | 351/245 |
| 6,290,357 B1 | 9/2001 | Massengill et al. | 351/209 |
| 6,321,338 B1 | 11/2001 | Porras et al. | 713/201 |
| 6,359,601 B1 | 3/2002 | Maguire, Jr. | 345/7 |
| 6,364,486 B1 | 4/2002 | Ball et al. | 351/203 |
| 6,386,706 B1 | 5/2002 | McClure et al. | 351/237 |
| 6,406,437 B1 | 6/2002 | Zur et al. | 600/558 |
| 6,431,708 B2 | 8/2002 | Krebs | 351/203 |
| 6,443,977 B1 | 9/2002 | Jaillet | 607/88 |
| 6,464,356 B1 | 10/2002 | Sabel et al. | 351/203 |
| 6,519,703 B1 | 2/2003 | Joyce | 713/201 |
| 6,540,355 B1 | 4/2003 | Couture | 351/203 |
| 6,578,966 B2 | 6/2003 | Fink et al. | 351/239 |
| 6,592,221 B1 | 7/2003 | Stregova | 351/203 |
| 6,656,131 B2 | 12/2003 | Alster et al. | 600/558 |
| 6,688,746 B2 | 2/2004 | Malov | 351/239 |
| 6,742,892 B2 | 6/2004 | Liberman | 351/203 |
| 6,769,770 B2 | 8/2004 | Fink et al. | 351/239 |
| 6,926,660 B2 | 8/2005 | Miller | 600/9 |
| 6,990,377 B2 | 1/2006 | Gliner | 607/54 |
| 7,004,912 B2 | 2/2006 | Polat | 600/558 |
| 7,104,659 B2 | 9/2006 | Grier et al. | 359/614 |
| 7,220,000 B2 | 5/2007 | Alster et al. | 351/224 |
| 7,275,830 B2 | 10/2007 | Alster et al. | 351/223 |
| 7,309,128 B2 | 12/2007 | Cappo et al. | 351/224 |
| 7,367,671 B2 | 5/2008 | Sabel | 351/203 |
| 2002/0024634 A1 | 2/2002 | Fink et al. | 351/237 |
| 2002/0047987 A1 | 4/2002 | Massengill et al. | 351/204 |
| 2002/0087201 A1 | 7/2002 | Firlik et al. | 607/45 |
| 2002/0107960 A1 | 8/2002 | Wetherall et al. | 709/225 |
| 2002/0186179 A1 | 12/2002 | Knowles | 345/8 |
| 2003/0020873 A1 | 1/2003 | Fink et al. | 351/200 |
| 2003/0090439 A1 | 5/2003 | Spitzer et al. | 345/8 |
| 2003/0156254 A1 | 8/2003 | Turovetsky | 351/203 |
| 2003/0214630 A1 | 11/2003 | Winterbotham | 351/203 |
| 2004/0012758 A1 | 1/2004 | Lin | 351/203 |
| 2004/0046934 A1 | 3/2004 | Sponsel et al. | 351/200 |
| 2004/0051848 A1 | 3/2004 | Gotze et al. | 351/203 |
| 2004/0075811 A1 | 4/2004 | Liberman | 351/203 |
| 2004/0100616 A1 | 5/2004 | Eremeev | 351/203 |
| 2004/0257528 A1 | 12/2004 | Miyake et al. | 351/203 |
| 2005/0001980 A1 | 1/2005 | Spector | 351/203 |
| 2005/0004624 A1 | 1/2005 | Gliner et al. | 607/54 |
| 2005/0041208 A1 | 2/2005 | Winterbotham | 351/203 |
| 2005/0122477 A1 | 6/2005 | Alster et al. | 351/237 |
| 2005/0213033 A1 | 9/2005 | Sabel | 351/203 |
| 2005/0213034 A1 | 9/2005 | Nagayoshi | 351/203 |
| 2005/0213035 A1 | 9/2005 | Yoshimeki et al. | 351/203 |
| 2006/0092377 A1 | 5/2006 | Sabel et al. | 128/898 |
| 2006/0283466 A1 | 12/2006 | Sabel | 128/898 |
| 2006/0288258 A1 | 12/2006 | Lo et al. | 714/46 |
| 2006/0290885 A1 | 12/2006 | Covannon et al. | 351/212 |
| 2007/0038142 A1 | 2/2007 | Todd et al. | 600/558 |
| 2007/0121070 A1 | 5/2007 | Alster et al. | 351/224 |
| 2007/0171372 A1 | 7/2007 | Seal et al. | 351/245 |
| 2007/0182928 A1 | 8/2007 | Sabel | 351/224 |
| 2007/0216865 A1 | 9/2007 | Sabel et al. | 351/203 |
| 2008/0013047 A1 | 1/2008 | Todd et al. | 351/203 |
| 2008/0024724 A1 | 1/2008 | Todd | 351/222 |
| 2008/0043201 A1 | 2/2008 | Todd | 351/222 |
| 2008/0077437 A1 | 3/2008 | Mehta et al. | 705/2 |

FOREIGN PATENT DOCUMENTS

| | | |
|---|---|---|
| DE | 10207839 | 9/2002 |
| EP | 115263 | 8/1984 |
| EP | 128783 | 12/1984 |
| EP | 135736 | 8/1985 |
| EP | 0242723 | 10/1987 |
| EP | 0537945 A1 | 4/1993 |
| EP | 544631 | 6/1993 |
| EP | 689822 | 1/1996 |
| EP | 775464 | 5/1997 |
| EP | 830839 | 3/1998 |
| EP | 1186271 | 3/2002 |
| EP | 1236432 | 9/2002 |
| EP | 1236433 | 9/2002 |
| EP | 1384462 | 1/2004 |
| EP | 1402869 | 3/2004 |
| EP | 1403680 A1 | 3/2004 |
| GB | 1465561 | 2/1977 |
| WO | WO 8000405 | 3/1980 |
| WO | WO 8810088 | 12/1988 |
| WO | WO 9100553 | 1/1991 |
| WO | WO 9110393 | 7/1991 |
| WO | WO 9200037 | 1/1992 |
| WO | WO 9517227 | 6/1995 |
| WO | WO 9700653 | 1/1997 |
| WO | WO 9811819 | 3/1998 |
| WO | WO 9849992 | 11/1998 |
| WO | WO 9952419 | 10/1999 |
| WO | WO 9959461 | 11/1999 |
| WO | WO 0012042 | 3/2000 |
| WO | WO 0036971 | 6/2000 |
| WO | WO 0113859 | 3/2001 |
| WO | WO 0145630 | 6/2001 |
| WO | WO 0147463 | 7/2001 |
| WO | WO 0180808 | 11/2001 |
| WO | WO 0209578 | 2/2002 |
| WO | WO 02/39754 | 5/2002 |
| WO | WO 02053072 | 7/2002 |
| WO | WO 03002070 | 1/2003 |
| WO | WO 03002190 | 1/2003 |
| WO | WO 03007944 | 1/2003 |
| WO | WO 03020195 | 3/2003 |
| WO | WO 03041630 | 5/2003 |
| WO | WO 03065964 | 8/2003 |
| WO | WO 03092482 | 11/2003 |
| WO | WO 03092570 | 11/2003 |
| WO | WO 03098529 | 11/2003 |
| WO | WO 2004066900 | 8/2004 |
| WO | WO 2005004985 | 1/2005 |
| WO | WO 2005037177 | 4/2005 |
| WO | WO 2005044096 | 5/2005 |
| WO | WO 2005063153 | 10/2005 |
| WO | WO 2005092270 | 10/2005 |
| WO | WO 2005110326 | 11/2005 |
| WO | WO 2005122872 | 12/2005 |
| WO | WO 2006/002070 | 1/2006 |
| WO | WO 0239754 | 1/2006 |
| WO | WO 2006006563 | 1/2006 |
| WO | WO 2006002070 | 5/2006 |
| WO | WO 2007/003902 | 1/2007 |
| WO | WO 2007109724 | 9/2007 |

WO WO 2008/077440 7/2008

OTHER PUBLICATIONS

Erich Kasten et al., Computer-based training for the treatment of partial blindness, Nature Medicine, vol. 4, No. 9, p. 1083-1087, Sep. 1998.

Burkhard Pleger et al., Functional magnetic resonance imaging mirrors recovery of visual perception after repetitive tachistoscopic stimulation in patients with partial cortical blindness, Neuroscience Letters, vol. 335, p. 192-194, Sep. 3, 2003.

Walter Widdig et al., Repetitive visual stimulation: A neuropsychological approach to the treatment of cortical blindness, NeuroRehabilitation, vol. 18, p. 227-237, Sep. 3, 2003.

Robert Sekuler, Vision Loss in an Aging Society: A Multidisciplinary Perspective/Vision Rehabilitation: Assessment, Intervention and Outcomes/The Lighthouse Handbook on Vision; Aug. 1, 2001, Gerontologist 556, vol. 41, Issue 4; ISSN: 0016-9013, © 2001.

Erich Kasten, Dorothe A. Poggel, Bernhard A. Sabel, Computer Based Training Stimulus Detection Improves Color and Simple Pattern Recognition in the Defective Field of Hemianopic Subjects; Nov. 1, 2000, Journal of Cognitive Neuroscience 1001, ISSN: 0898-929X; vol. 12, Issue 6; ©, Nov. 1, 2000.

Rewiring Your Gray Matter: The brain: You can trach an old brain new tricks. Neuroplasticity promises to give a whole new meaning to 'changing your mind'; Jan. 1, 2000, Newsweek 63; ISSN: 0028-9604; vol. 134, Issue 26, ©, Jan. 1, 2000.

Teaching the brain to restore sight; Popular Mechanics, Jan. 18, 1999, Associated Press Newswires, © 1999.

Philip A. Schwartzkroin, Synaptic Plasticity: Molecular, Cellular, and Functional Aspects (book reviews); May 20, 1994, Science 1179; vol. 264, No. 5162, ISSN: 0036-8075; © 1994.

J. Zihl, et al., Restitution of visual function in patients with cerebral blindness; Zihl and von Cramon, J Neurol Neurosurg Psychiatry, May 1, 1979.

J. Zihl, et al. Restitution of visual field in patients with damage to the geniculostriate visual pathway; Zihl and von Cramon, Human Neurobiology, Jun. 1, 1982.

E. Kasten, S. Wuest, B. Sabel, Journal of Clinical and Experimental Neuropsychology 1998, vol. 20, No. 5, pp. 581-598 "Residual Vision in Transition Zones in Patients with Cerebral Blindness", Aug. 5.

F. Schmielau, Restitution of visual function in cases of brain damaged patients: Efficacy of localization specific sensory and sonsomotoric rehabilitation procedures. In "Psychologie in der Neurologie" [Psychology in Neurology], P. Jacobi (editor). Berlin: Springer, 115-126, Jun. 1, 1989.

E. Kasten et al., Restoration of vision II: Residual functions and training-induced visual field enlargement in brain-damaged patients, Jun. 1, 1999.

K.K. ball, et al, Journal of the Optical Society of America A, vol. 5, No. 12, pp. 2210-2219 "Age and Visual Search: Expanding the Useful Field of View", Jun. 3, 1989.

E. Kasten, et al., Spatial Vision, vol. 10, No. 4, pp. 499-503, "Programs for Diagnosis and Therapy of Visual Field Deficits in Vision Rehabilitation", Aug. 3, 1997.

E. Kasten, et al., Restorative Neurology and Neurology and Neuroscience, vol. 8, No. 3, pp. 113-127, "Visual Field Enlargement After Computer Training in Bran-damaged Patients Whit Homonymous Deficits: An Open Pilot Trial", Aug. 1, 1995.

Alan Cowley, Alan Cowley, Perimetric Study of Field Defects in Monkeys After Cortical and Retinal Ablations, Quarterly Journal of Experimental Psychology, pp. 232-245, Dec. 18, 1967.

New Research on the Efficacy of NoveVision VRT Presented at 32nd Annual North American Neuro-Ophthalmology Society Meeting; Mar. 2, 2006, Business Wire © 2006.

Sharon Begley, Training the brain to see again; Sharon Begley, May 1, 2005, Saturday Evening Post, vol. 277; Issue 3; ISSN: 00489239; © 2005 Bell & Howell Information and Learning Company.

In-Sung Yoo, Advances in Medicine: New therapy gives hope to stroke victims; In-Sung Yoo, Mar. 1, 2005, The New Journal, © 2005, The New Journal.

Sharon Begley, Stroke patients have hope in sight; As part of the revolution in neurobiology, doctors are trying to train healthy brain cells to take over the visual function of neurons damaged by a stroke; Sharon Begley, Wall Street Journal, Feb. 4, 2005, The Globe and Mail.

John Dorschner, Stroke victims improve vision with computer therapy; John Dorschner, Knight Ridder Newspapers, Jul. 19, 2004, The Tallahassee Democrat, © 2004.

Kelts, et al., "*Training—induced perceptual recovery after visual cortical stroke,*" Department of Ophthalmology and the Center for Visual Science, University of Rochester, 1 page. Mar 1, 1999.

\* cited by examiner

Higher Luminosity Green

Low Luminosity Background

Higher Luminosity Yellow

Low Luminosity Background

Higher Luminosity Yellow

Low Luminosity Background

Close-up view, Time = 0 ms

Higher Luminosity Yellow

Higher Luminosity Green

Low Luminosity Background

Time = 250 ms

Higher Luminosity Yellow

Higher Luminosity Green

Low Luminosity Background

Time = 500 ms

Higher Luminosity Yellow

Higher Luminosity Green

Low Luminosity Background

Time = 760 ms

Higher Luminosity Yellow

Higher Luminosity Green

Low Luminosity Background

Time = 2000 ms

Time = 2250 ms

Higher Luminosity Orange

Higher Luminosity Green

Low Luminosity Background

Time = 2500 ms

Higher Luminosity Yellow

Higher Luminosity Green

Low Luminosity Background

FREQUENCY DOUBLING FIXATION STIMULI FOR VISUAL FIELD TESTING AND THERAPY

CROSS REFERENCE TO RELATED APPLICATIONS

This patent application claims priority from U.S. Provisional Application Ser. No. 60/833,199 filed on Jul. 25, 2006 and U.S. Provisional Application Ser. No. 60/867,499 filed on Nov. 28, 2006, which are incorporated by reference herein in their entirety.

TECHNICAL FIELD

The present invention relates to systems for maintaining the focus of a subject on a specified region of a display for purposes of testing or improving a subject's vision.

BACKGROUND

The macula is the region of the retina which is used for high acuity vision, as is typically required for reading. To diagnose macular damage, a patient may undergo various types of examinations, including automated perimetry or campimetry, in which the patient is positioned in front of a test surface and is asked to maintain focus on a target. A computer then actuates one or more light sources to present visual stimuli at specific points on the test surface. The patient is asked to press a button in response to perceived test stimuli and the examiner or computer records the patient input and associated spatial information. In this way a visual field map is created.

The human retina is unable to fixate continuously upon an unmoving, unchanging stimulus. After less than a second of stimulation, the subject's retinal cells will adapt to the stimulus and no longer relay any information to the brain regarding the stimulus. Such adaptation is problematic for devices requiring constant fixation upon a fixed point since the viewer must change fixation in order to continue seeing the object of regard. This changing fixation may reduce the accuracy, precision, and overall effectiveness of testing, therapeutic, or non-therapeutic visual stimulation programs that require continuous unchanging visual fixation.

The human visual system includes two simultaneously functioning pathways. The more primitive "M" pathway is dedicated largely to the recognition of moving objects or objects that change in luminosity. The "P" pathway is more evolved and more closely coupled to neural structures associated with conscious thought. The "P" pathway provides recognition of fine detail and color to the brain and is much less committed to motion detection.

In persons who have suffered damage to the visual system (which includes the brain itself), these two pathways frequently are affected to different degrees. Moreover, the two systems usually recover function at different rates. This disparity of functional loss and recovery can cause significant disharmony of the innately matched systems and resulting disturbances to the overall sensory function of the subject.

The ability to accurately detect the different types of visual processing disturbance and to properly treat the affected pathways is of vital importance to the treating practitioner and ultimately, the patient. Increased diagnostic testing sensitivity and visual therapy specificity result in better prognosis for recovery of the individual's function. Current diagnostic testing modalities are limited in their ability to detect specific types of visual function damage.

Most field-of-vision testing falls into one of two categories: Static perimetry and kinetic perimetry. Static perimetry is valuable in establishing a depiction of fine light sensitivity or detail within the central 30 to 60 degrees of visual field ("P" cell function), while kinetic perimetry is valuable in identifying the borders of motion vision function ("M" cell function). However, neither technique is able to identify efficiently the amount or level of motion sensitivity at all the points within the borders.

In static perimetry, the patient fixates upon a specific point while light stimuli (spots) are delivered to various points in the peripheral visual field. Static perimetry can be administered using peripheral stimuli of varying brightness to determine the level of luminance sensitivity throughout the field, or with peripheral stimuli of identical brightness, to screen for the presence or absence of vision at various locations.

Kinetic perimetry also requires a patient to fixate a central spot during delivery of peripheral stimuli. In kinetic perimetry, the stimuli are luminous spots of varying size and brightness. The spots are moved from an area where there is known to be no vision (e.g. the far periphery or physiologic blind spot) toward areas where vision may exist. The patient is tasked with responding upon detection of a moving light in the periphery. Test points are delivered along radii of the circle (or "horopter") of the patient's field of vision. The points of first detection are recorded on a plot and the circumference of the connected points is considered the border of motion and light sensitivity for the brightness and size of the stimulus used.

Frequency doubling technology (FDT) is used to test the spatial resolution of a subject's visual field. In FDT, a subject attempts to observe a peripheral square or circular grating comprised of striations of alternating luminosities. The gratings are modulated in a wave pattern involving temporal changes in luminosity of the striations. The luminosity modulation is performed above the critical flicker frequency (CFF), typically about 25 Hz, so that the modulation is not noticeable to the subject. If the subject's visual field is sufficient, the subject will observe an optical illusion in which the spatial frequency of the striations is doubled, i.e., the space between the striations is halved. The spatial frequency or contrast may be modulated to determine the limits of the subject's spatial resolution. In a patient with visual field damage, e.g., one suffering from glaucoma, an abnormally low spatial frequency may be required for the subject to observe the frequency doubling illusion. In U.S. Pat. No. 6,068,377, issued May 30, 2000 to McKinnon, an alternate version of FDT is employed, in which the grating is isoluminous, but with alternating hue.

Work in the laboratory of Krystel R. Huxlin at the University of Rochester has utilized a series of spot stimuli for visual field therapy. In the poster presentation, "Training-induced perceptual recovery after visual cortical stroke" Eric Kelts, Jennifer M. Williams, Brad Feldman, Mary Hayhoe and Krystel R. Huxlin, 30$^{th}$ Annual NANOS meeting, Orlando, Fla., 2004, stimuli move with respect to the entire visual field. Such an approach is not consistent with visual restoration therapy approaches that individually target small regions of the visual field. Additionally, movement of a stimulus across a large region will tend to cause distraction of a patient, and is thus inconsistent with visual therapy approaches that utilize a fixation stimulus. If patient feedback were collected with such a system, it would be difficult or even impossible to precisely locate the visual field region that caused the patient's perception to be triggered.

SUMMARY OF THE INVENTION

In accordance with an embodiment of the invention, alteration of a fixation stimulus displayed on a computer-driven display allows a human subject to maintain extended visual fixation upon the resulting dynamic stimulus. The fixation is presented upon the display and the stimulus is altered to allow resensitization of the subject's retina, thereby allowing prolonged visual fixation upon the resulting dynamic target.

In accordance with various embodiments, the steps of presenting the stimulus and altering the stimulus may be repeated for a given number of cycles to allow sustained sensitization and prolonged fixation by the subject. The fixation of the subject may be verified by presenting a test cue and recording a subject's input in response to the test cue. Like the dynamic fixation stimulus, the test cue may also be altered to allow resensitization of the subject's retina.

In order to prevent the subject from predicting the time at which a test cue is presented, successive presentation of the test cue may be performed with varying intervening time intervals. One way to vary the time intervals is to vary the number of cycles of presentation of the fixation stimulus and the altered fixation stimulus.

In accordance with particular embodiments, the alteration of the dynamic fixation stimulus is visible only by using a portion of the subject's retina corresponding to about 2 degrees or less of the subject's central visual field.

There are many suitable fixation stimulus geometries and dynamic transformations. For example, the fixation stimulus may have the form of a repetitively translating object, a rotating object, or an intermingled set of cyclically changing objects. The stimulus could include two sets of intermingled striations of opposite and cyclically altering luminosities.

In embodiments of the invention, the dynamic fixation stimulus is used for purposes of vision testing or training.

In related embodiments, a method is provided for stimulating a motion-detecting visual pathway of a subject. A subject is tasked with fixating on a central stimulus displayed on a computer-driven display. While the subject is visually fixated, a peripheral stimulus is presented on the display. At least one characteristic of the peripheral stimulus is altered so as to trigger the motion-sensitive visual pathway of the subject.

In other related embodiments, the altered characteristic may be the spatial locus, size, pattern, luminosity or hue of the stimulus. The altered and base stimulus may be alternately displayed in a cyclical manner to sustain the display of a dynamic peripheral stimulus. While alternately displaying the base and altered stimulus, the subject's response, indicative of their detection of the stimulus, may be monitored and recorded. The dynamic peripheral stimulus may be, for example, a repetitively translating object, or a repetitively blinking object. By first determining the bounds of a subject's visual field, testing or therapy can be concentrated within those bounds.

In further related embodiments, a computer program product for use on a computer system is provided for stimulating motion-sensitive regions of a subject's peripheral vision. The computer program includes a computer usable medium having computer readable program code, which includes program code for providing a dynamic peripheral stimulation displayed upon a computer-driven display and program code for recording the subject's response to the dynamic peripheral stimulation.

In accordance with another embodiment of the invention, a method is provided for maintaining fixation for purposes of testing or treating the visual field of a subject; the method may also be implemented in a computer system or computer program product. The method includes the steps of providing a fixation stimulus for the subject to visually fixate upon, repeatedly altering the stimulus to create an optical illusion that is only detectable by use of the subject's central visual field and presenting a peripheral stimulus to the subject while the subject is fixated on the fixation stimulus. The subject's response to the peripheral stimulus may be recorded.

In related embodiments, the difficulty level of the optical illusion is tuned to match the spatial perception ability of the subject. The optical illusion may be a frequency doubling optical illusion, such as a frequency doubling grating. The difficulty level of the frequency doubling grating may be tuned by altering the spatial frequency of the grating. For example, the tuning process may include increasing the spatial frequency of the grating until the illusion is not properly detected by the subject and then maintaining the spatial frequency at a level that is detectable by the subject, yet near the limit of the spatial resolution of the subject's central visual field. The fixation stimulus may be systematically altered to target different retinal regions, for example, by rotation or translation, thereby preventing desensitization. A fixation test cue may be presented to query the subject's fixation upon the stimulus.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

Figure 1:
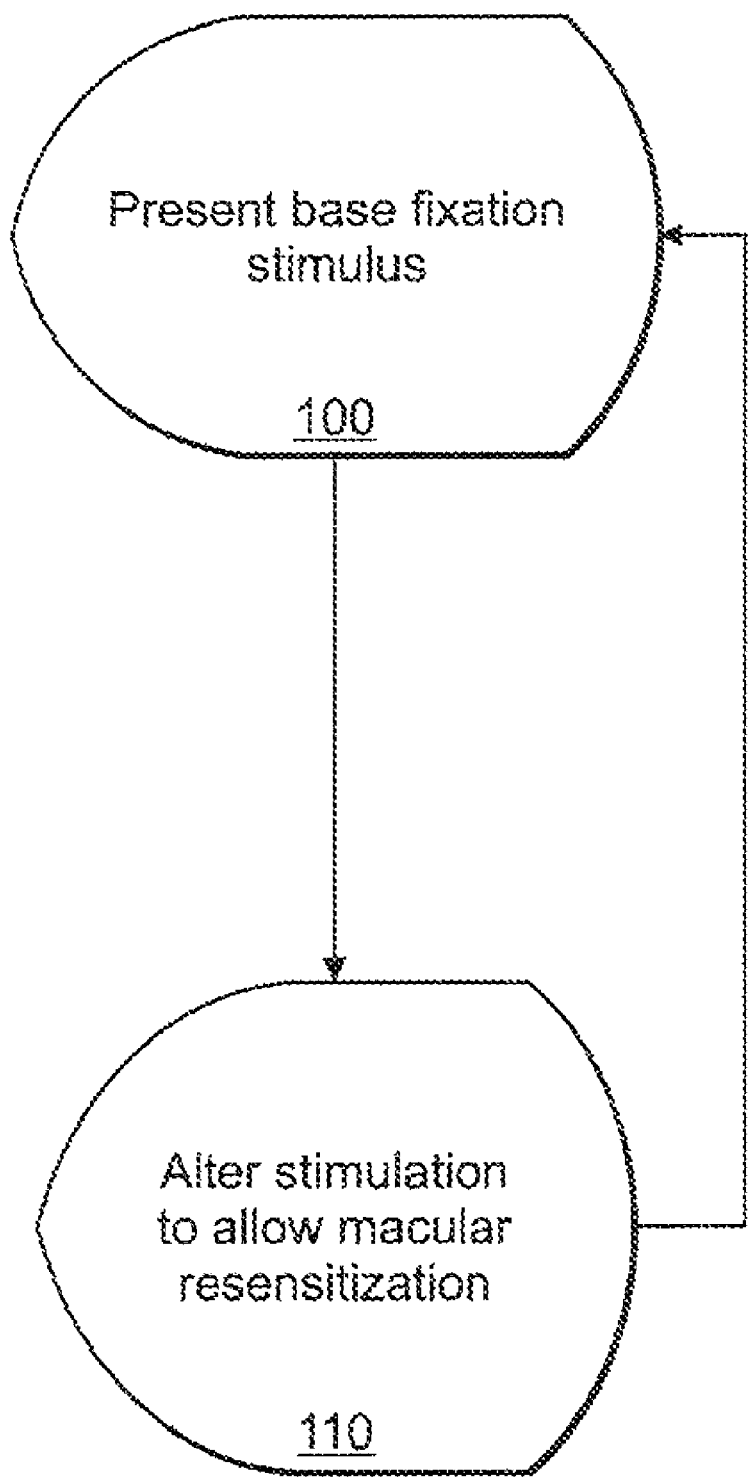
FIG. 1 shows a flow chart of a method for presenting a dynamic fixation stimulus in accordance with an embodiment of the invention.

Definitions. As used in this description and the accompanying claims, the following terms shall have the meanings indicated, unless the context otherwise requires:

"Visual Restoration Therapy" shall mean a process for allocating and targeting light stimuli to particular regions of a patient's visual field.

A "subject" shall mean a human receiving light stimuli during a visual restoration therapy session.

In illustrative embodiments of the invention, a dynamic stimulus is presented via a computer-driven display for a human subject (e.g., a patient or trainee) to fixate upon. At least a portion of the dynamic fixation stimulus is periodically altered in appearance, to mitigate the stimulation to corresponding retinal regions and facilitating retinal resensitization. Accordingly, the subject should be able to avoid retinal adaptation and sustain fixation upon the stimulus for longer than would typically be achievable or comfortable with a static stimulus. When used as a central target in perimetry, campimetry, or vision enhancing training (e.g. vision restoration therapy targeting peripheral regions), the dynamic fixation stimulus may help to increase the accuracy, precision, reproducibility, and effectiveness of the procedure. In some embodiments, the dynamic changes in the stimulus may only be observed using the central portion of a subject's visual field. Embodiments may be implemented using a computerized display with appropriate software routines according to methods disclosed herein. Computer based systems for implementing visual restoration therapy are commercialized by the assignee, NovaVision Inc. of Boca Raton, Fla. U.S. Pat. No. 6,464,356 and U.S. Patent Application publication nos. 2005-0213033, 2006-0092377, 2006-0283466, 2007-0038142 all disclose computer based systems for visual restoration therapy and are hereby incorporated by reference herein.

In related embodiments of the invention, a dynamic stimulus is used as a peripheral spot stimulus for purposes of visual field mapping or therapy. The dynamic peripheral stimulus is presented upon a region of a display to target a corresponding peripheral region of the visual field and preferentially activates the motion-detecting cells and/or structures (e.g., the M pathway) in that region of the visual field. When used with visual restoration therapy, perimetry, or campimetry, the dynamic peripheral stimulus allows measurement and/or therapeutic stimulation of motion-detection pathway function. Unlike stimuli of the prior art that move in a pattern across all or large portions of the visual field, dynamic peripheral stimuli of the present invention are confined to subregions of the visual field in a manner that makes them compatible with targeted stimulation of the M pathway in small regions that may be defined or located with respect to a fixation stimulus. Embodiments include using dynamic peripheral stimuli that are "animations" within narrowly bounded zones that are of a size comparable to traditional spot stimuli and moving the bounds of the animation to a second location. Patient responses to the animated stimuli may be recorded upon presentation of each dynamic peripheral stimulus.

FIG. 1 shows a flow chart, which summarizes a method in accordance with an embodiment of the invention. A base fixation stimulus is presented on a computer display (step 100). Although usually presented in the center of the display, the stimulus could also be presented off-center to better target a particular region of the visual field for testing or training. After presenting the base stimulus for a period of time, all or part of the stimulus is altered (step 110) in a manner that should allow resensitization of the subject's retina. The altered stimulus may be presented on a location of the display that is superimposed upon the base stimulus, or slightly offset, so that fixation may be readily maintained on the same area of the display. The area of fixation is typically small, relative to the size of the display (e.g., less than 5% or 1% of the display area). Resensitization may be accomplished by reducing the overall luminosity (brightness), or spectral distribution of luminosity (i.e., color) of all or part of the stimuli, which may advantageously lower stimulation of corresponding retinal regions. After presenting the altered stimulus for a time, one or more additional altered stimuli may be presented, or the base stimulus may presented again by repeating step 100. The resulting loop may be repeated for a number of iterations, until a condition is fulfilled (e.g., completion of testing, or adequate subject performance) or an interrupt is encountered. The timing of the presentation of the base and altered stimuli may be adjusted to minimize retinal desensitization; for example, stimuli may be switched on a subsecond basis. As a result of the repeated resensitizations, that part of the subject's visual field that detects the fixation stimulus should be in a condition of sustained sensitization, thereby allowing for prolonged fixation upon the stimulus.

The repetition between the base and alternate stimuli may cycle, for example, at a frequency between 0.5 and 100 Hz, and more particularly may be between 1 Hz and 10 Hz. For example, the cycle may have a frequency of about 3 Hz, with stimuli presented for period of about 150 ms. However, the cycles need not be regular; the delay between changes in the stimulus may vary from cycle to cycle, but the majority of such delays are typically consistent with the above ranges to allow for sustained sensitization. The delays could increase with time, decrease with time, follow a pseudo-random sequence, or other pattern. For example, the sequence of delays could be 210 ms, 240 ms, 275 ms, 255 ms, etc.

Figure 2:
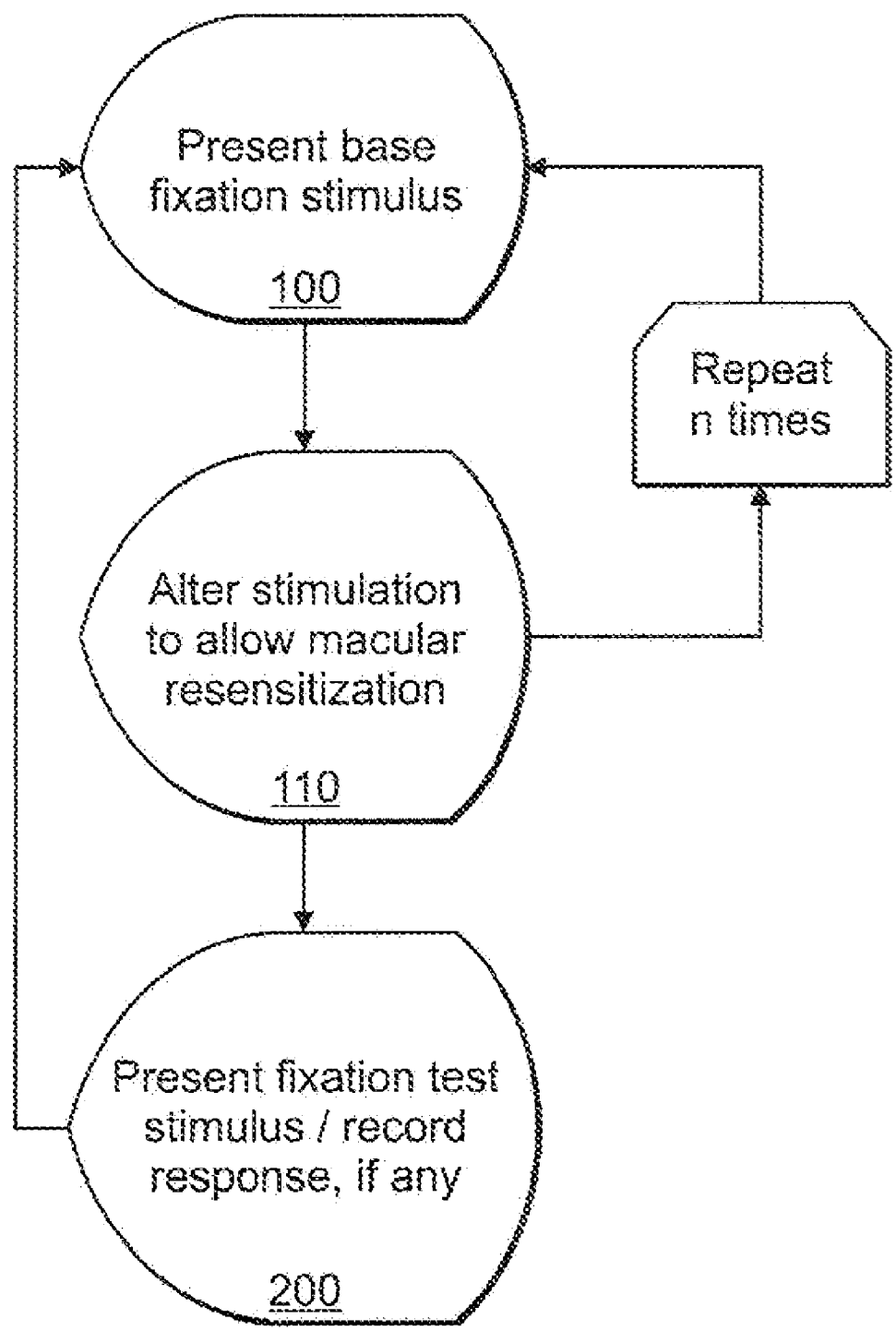
FIG. 2 shows a flow chart of a method for presenting a base and alternate dynamic fixation stimulus in accordance with an another embodiment of the invention.
Figure 3:
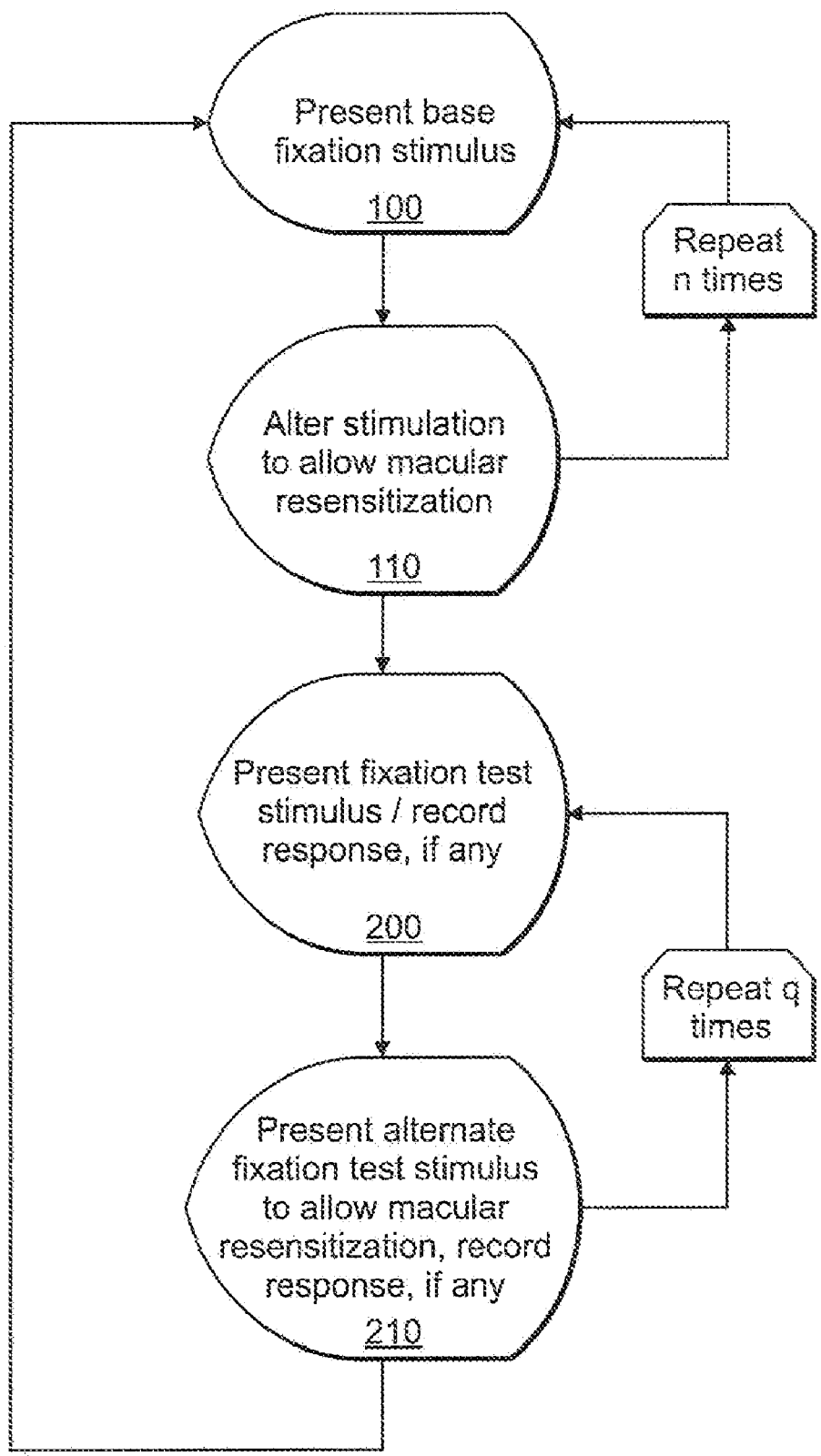
FIG. 3 shows a flow chart of a method for presenting a base and alternate dynamic fixation stimulus in accordance with the embodiment of FIG. 2.
Figure 4:
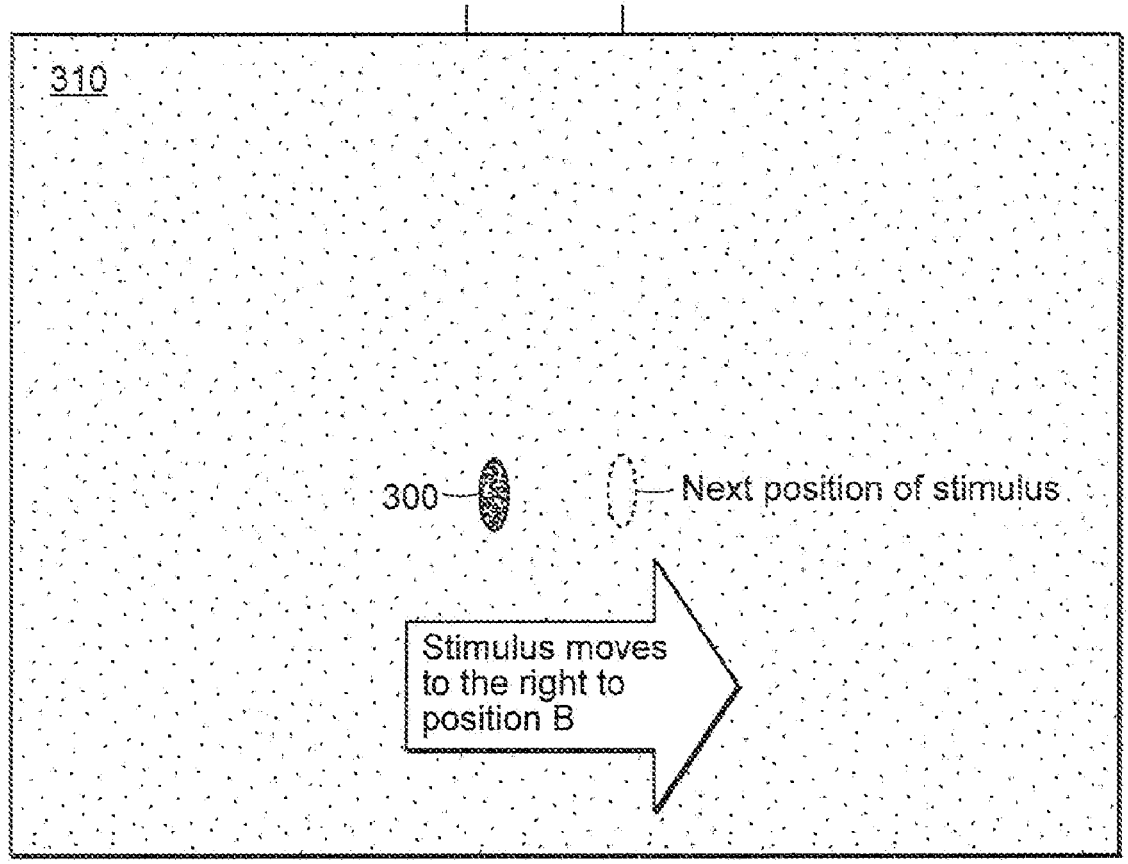
FIGS. 4-10 show a repetitively translating fixation stimulus in accordance with an embodiment of the invention.
Figure 4:
Figure 4:
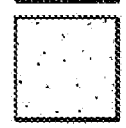
Figure 5:
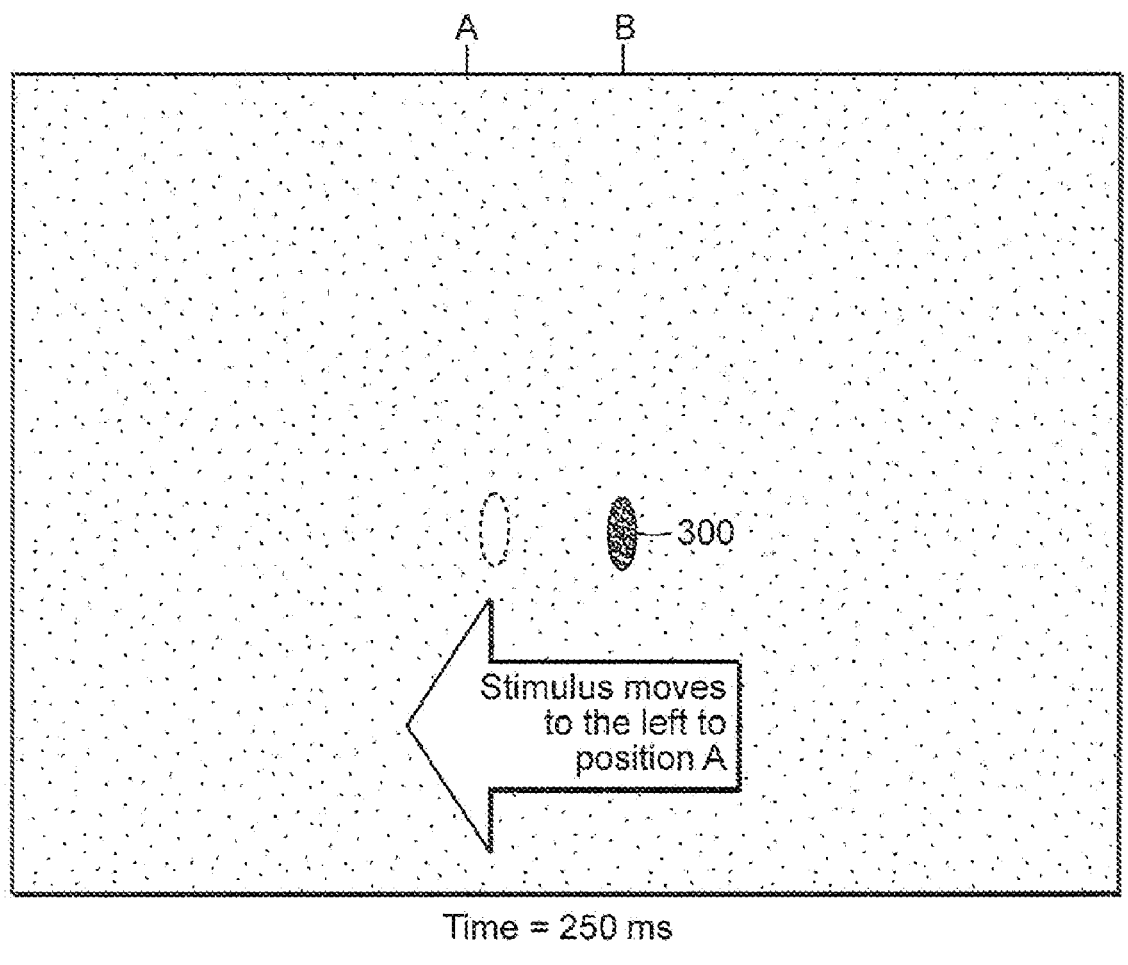
Figure 6:
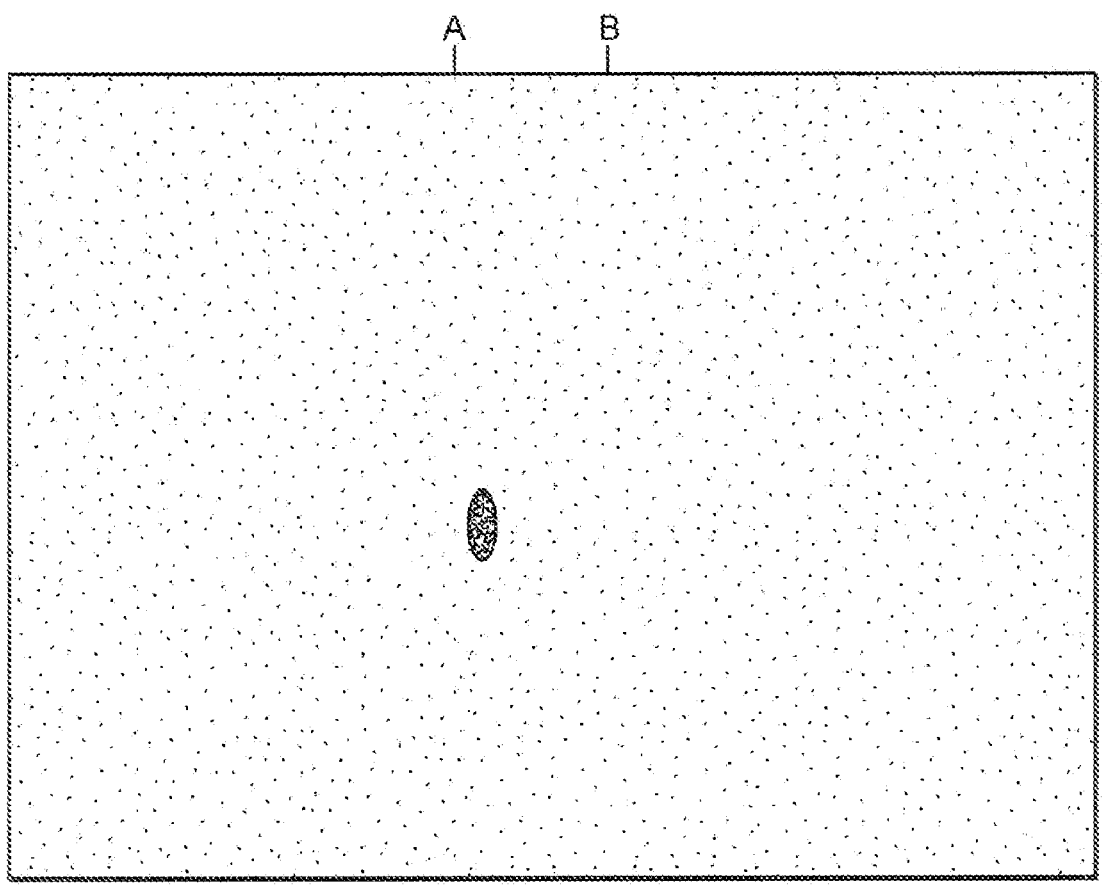

FIGS. 2-3 show flow charts corresponding to embodiments for presenting a dynamic fixation stimulus to a subject and testing the subject for fixation. As in the embodiment of FIG. 1, a loop is employed; a base stimulus is displayed for a time period (step 100), an altered stimulus (step 110) is displayed for a time period, and the process is repeated. After a given number (designated by the variable n) of loop cycles, a fixation test cue is presented (step 200). The test cue may consist of changing the shape, color, pattern or other visually detectable feature of the dynamic fixation stimulus. The subject may be instructed to respond to the test cue through a computer-input device, such as a keyboard, mouse, touchscreen, joystick, microphone, etc. Varying n between cycles of alternately presenting the fixation stimulus and test cue may advantageously cause the test cue to be presented at times that are not readily predictable by the subject, further ensuring subject compliance with regard to fixation. However, the timing of test cue presentation may be varied in other ways, including by altering the duration of base or alternate stimulus presentation. As shown in the flow chart of FIG. 3, the test cue may be altered (step 210) as well, to facilitate continued fixation upon the test cue. Responses may be received from the subject during periods in which either the test cue or altered test cue are displayed. The test cue and altered test cue may be alternately displayed in a loop (steps 200-210) which may repeat a number of times, designated by the variable q. As is true for determining n, q may be determined in a number of ways and may be either fixed or varied. For example, the test cue and alternate test cue may be iteratively displayed (steps 200-210) until a response is received from the subject or may simply be displayed for a given number of cycles, or for a given elapsed time. In any case, after the test cue presentation phase is complete, the base and altered fixation stimulus may again be displayed (steps 100-110).

FIGS. 4-10 schematically show, in time-sequence, an embodiment of a dynamic fixation stimulus and fixation test cue that utilizes a repetitively translating fixation stimulus presented on a computerized display. As shown, the translating stimulus 300 is a green oval which horizontally translates between a first position (position A, shown in FIGS. 4, 6, 7, and 10), and a second position (position B, shown in FIGS. 5, 8 and 9). Although shown as having a higher luminosity than its background 310, the translating stimulus may also be darker than the background. Generally, the translating stimulus should contrast sufficiently with the background so that it is detectable by the subject (though the level of contrast may also be varied during a procedure or course of therapy). Of course, the translating stimulus 300 need not be an oval, but could be a any of a variety of shapes and may translate horizontally, diagonally, or alternately in various directions or patterns. The stimulus 300 may have any of a variety of colors and patterns.

Figure 7:
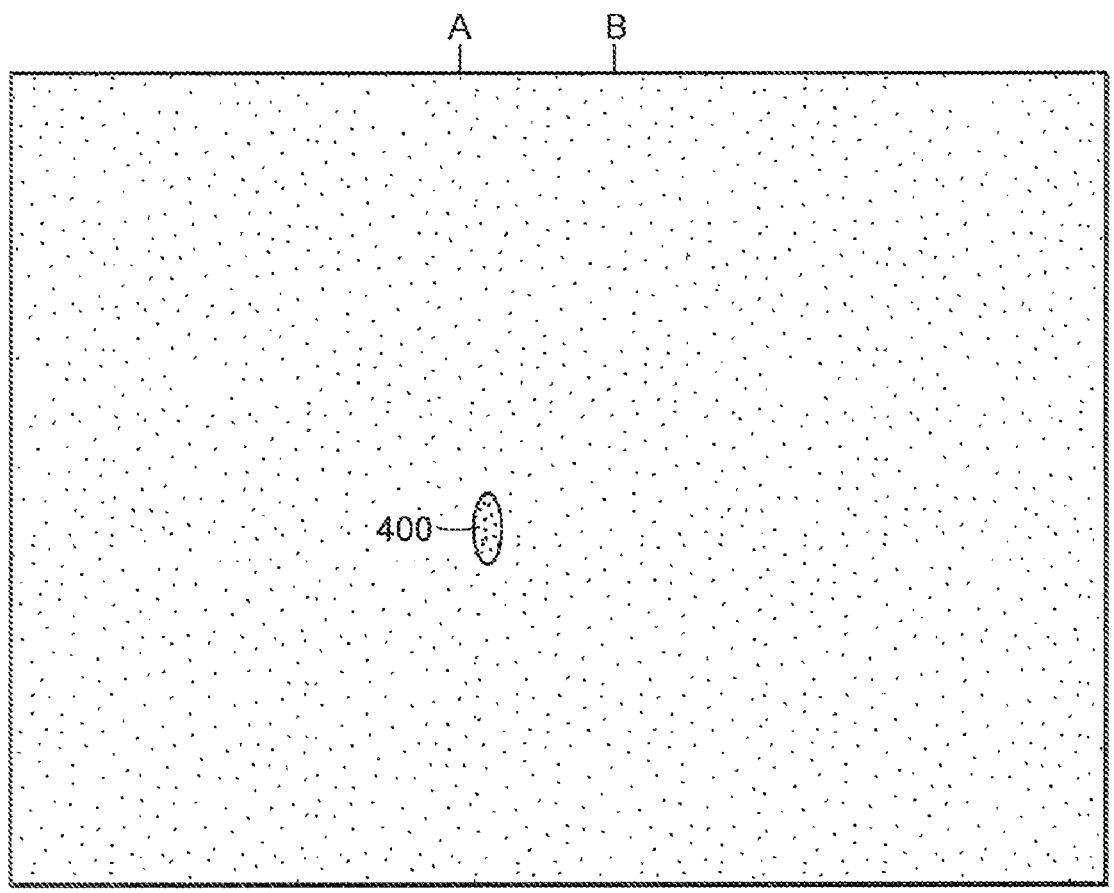
Figure 7:
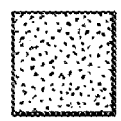
Figure 7:
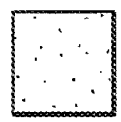
Figure 8:
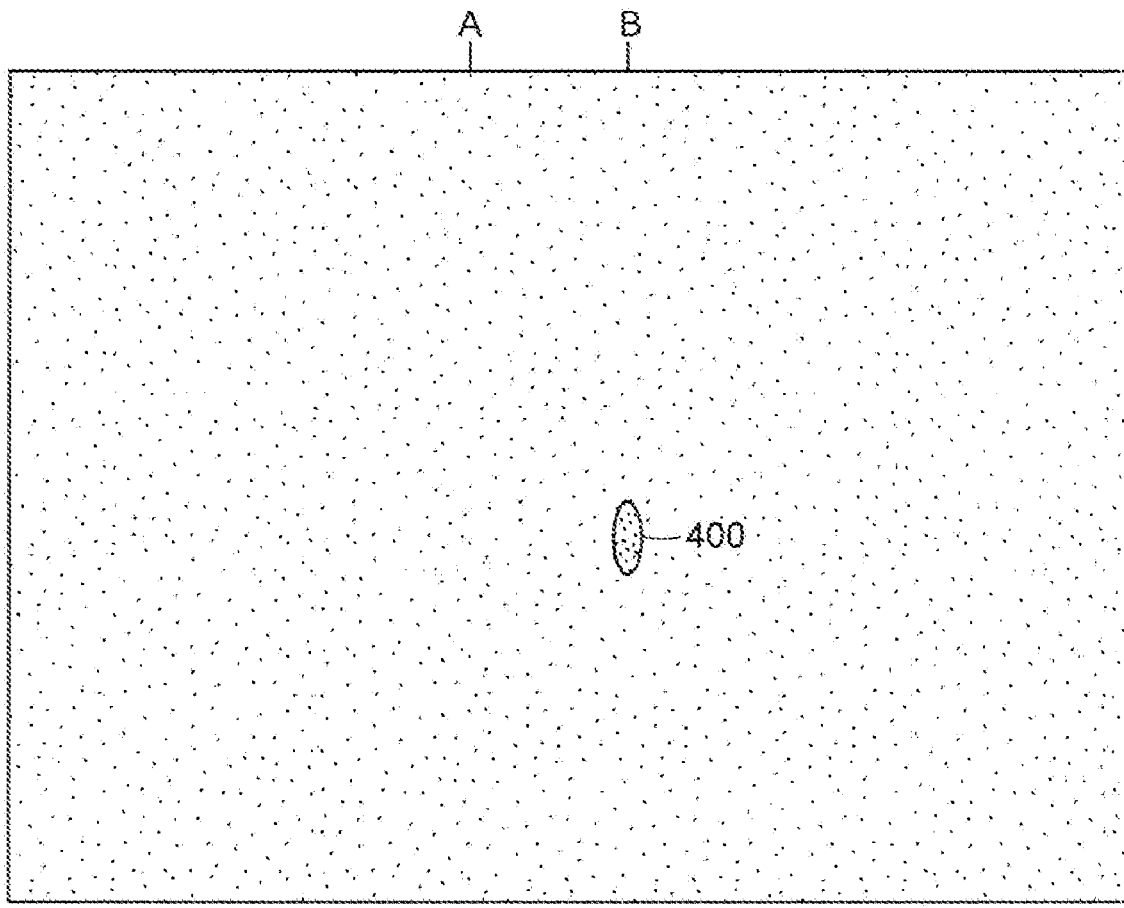
Figure 8:
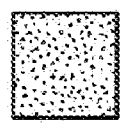
Figure 8:
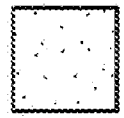
Figure 9:
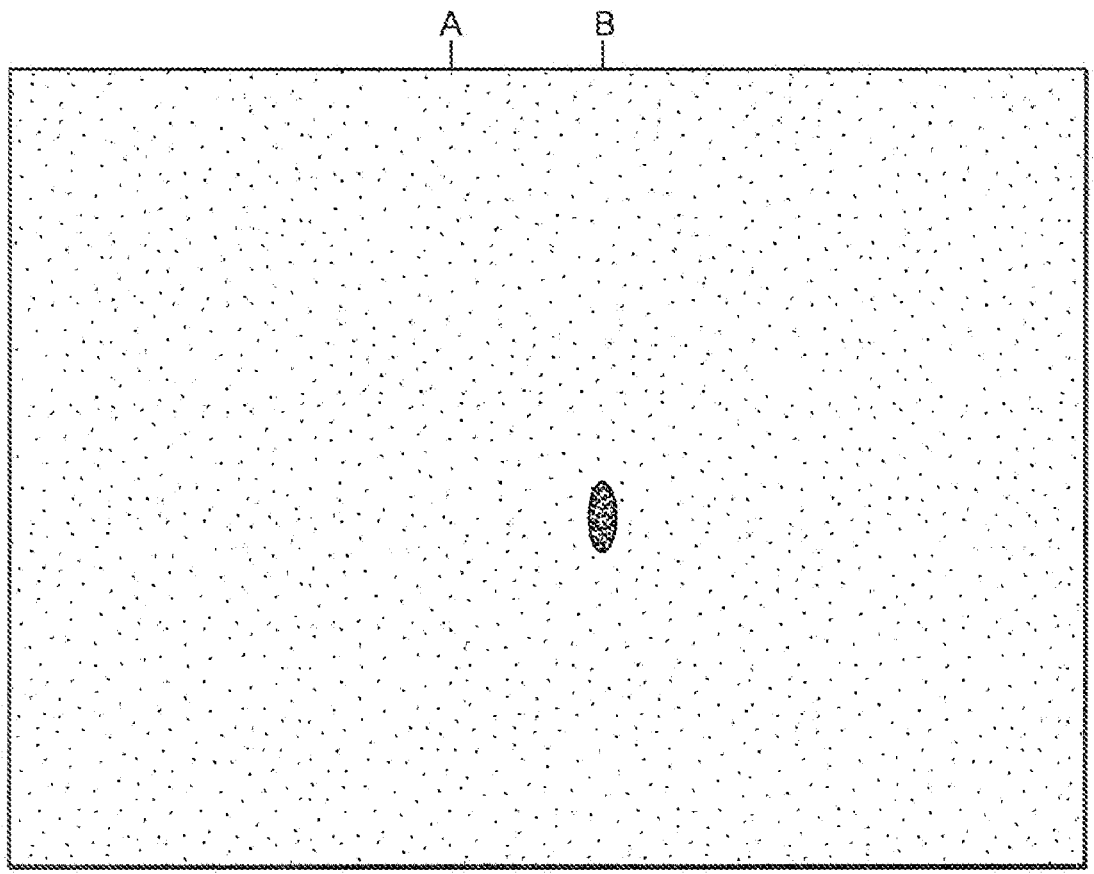
Figure 9:
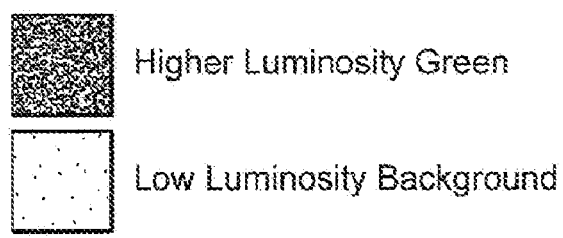
Figure 10:
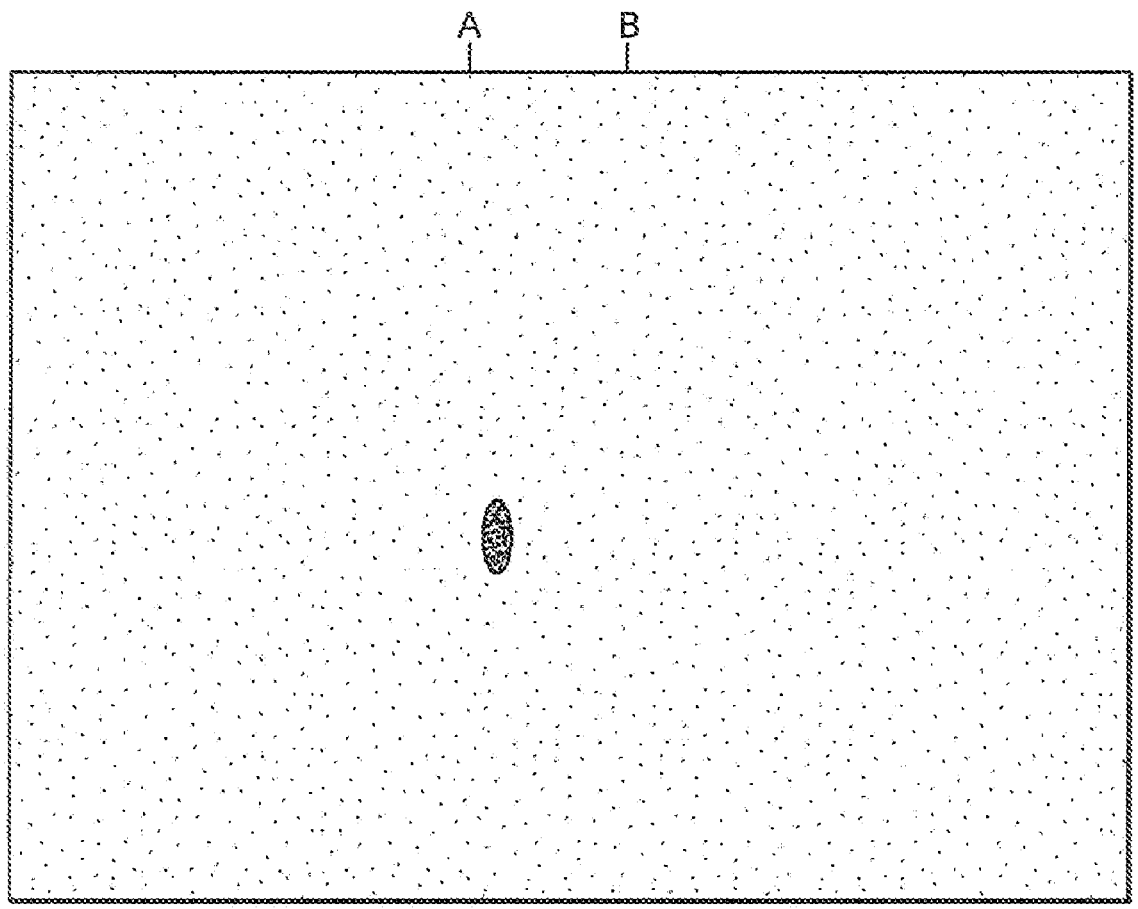
Figure 11:
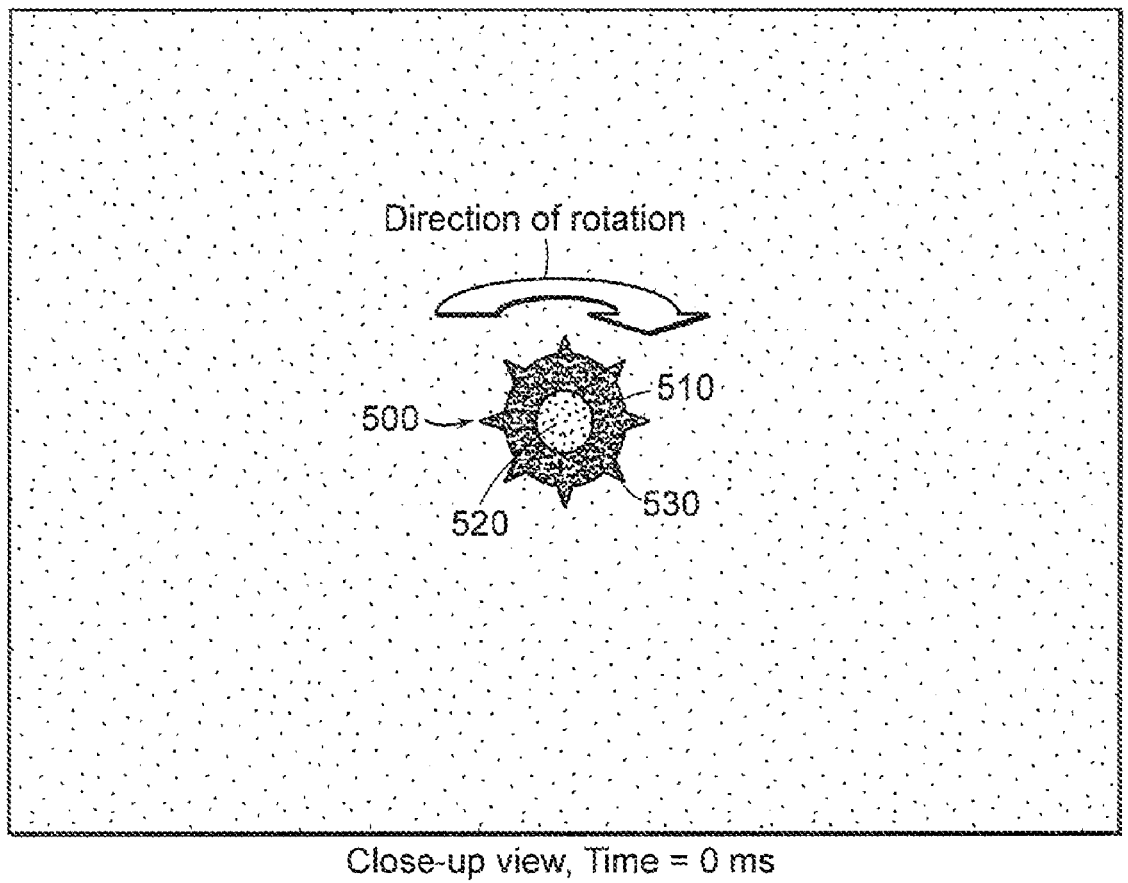
FIGS. 11-17 show a rotating fixation stimulus in accordance with another embodiment of the invention.
Figure 11:
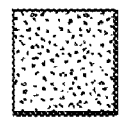
Figure 11:
Figure 11:
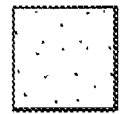
Figure 12:
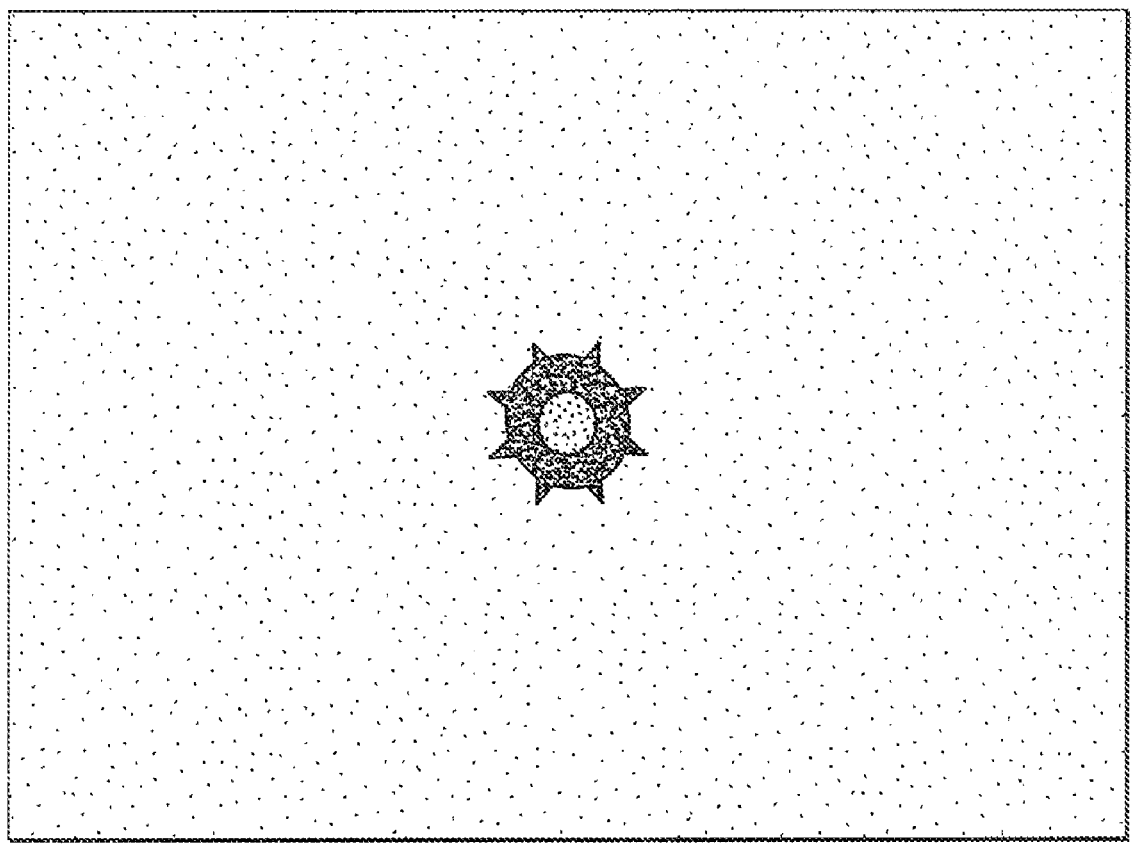
Figure 12:
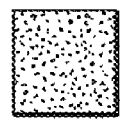
Figure 12:
Figure 12:
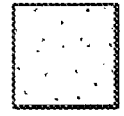
Figure 13:
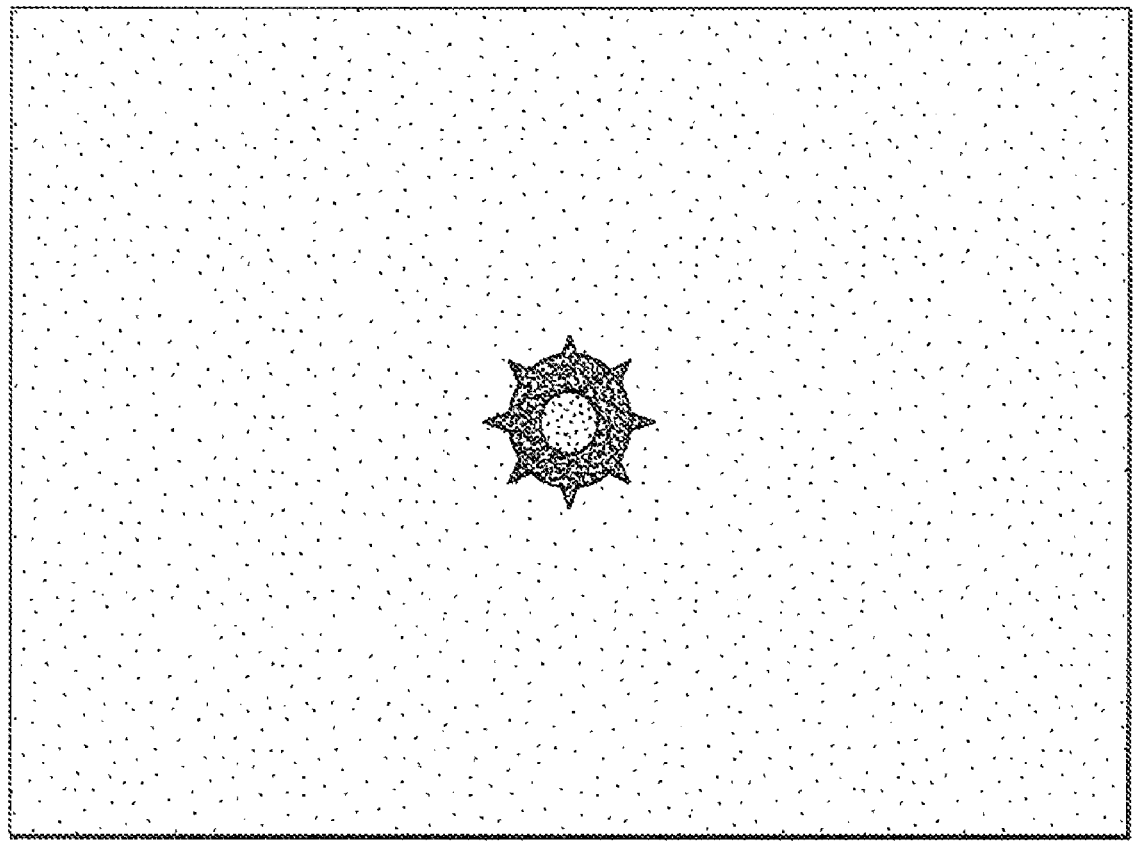
Figure 13:
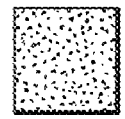
Figure 13:
Figure 13:
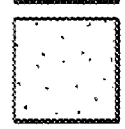
Figure 14:
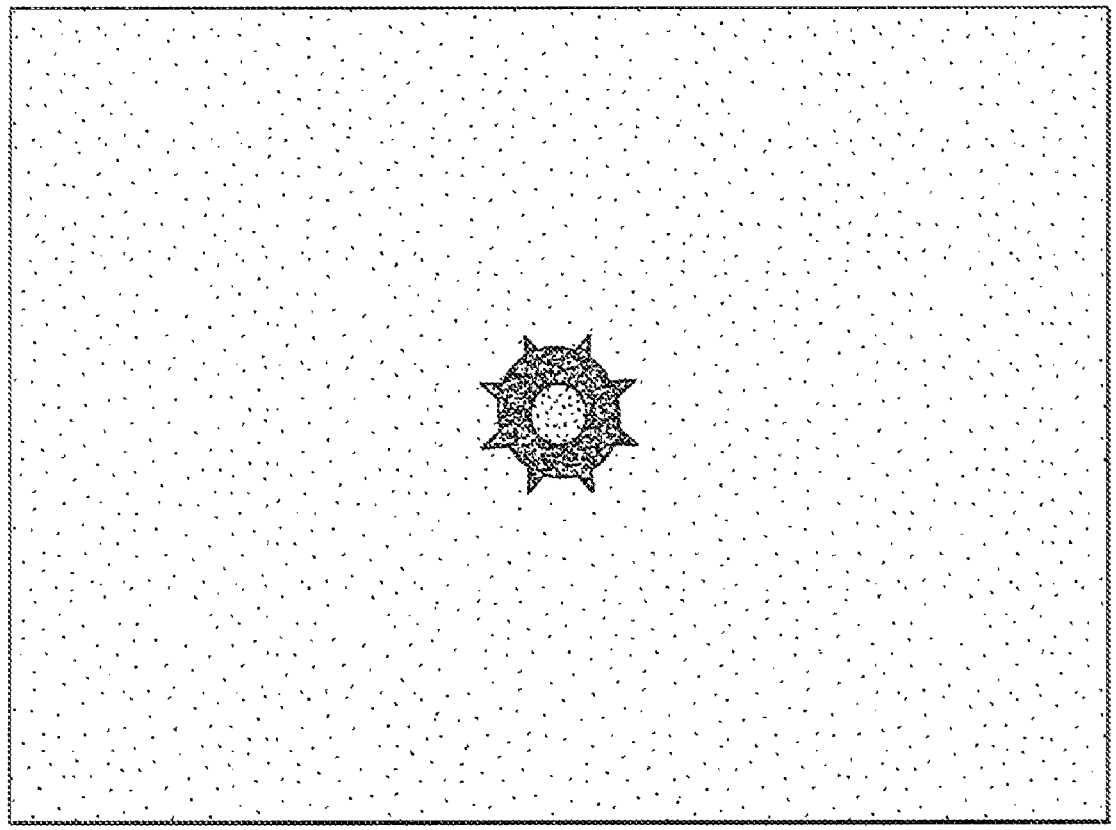
Figure 14:
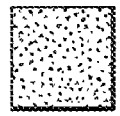
Figure 14:
Figure 14:
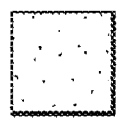
Figure 15:
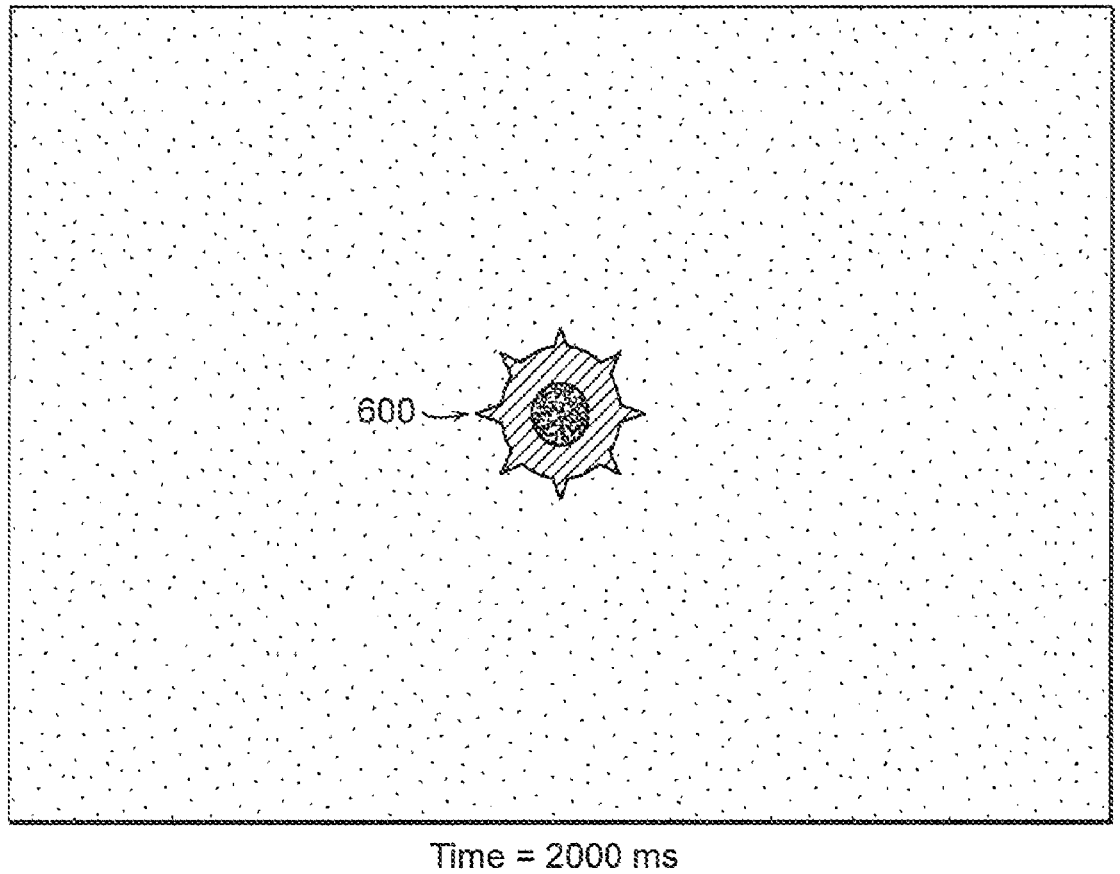
Figure 15:
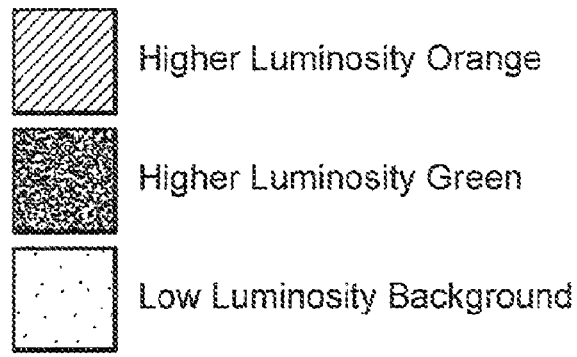
Figure 16:
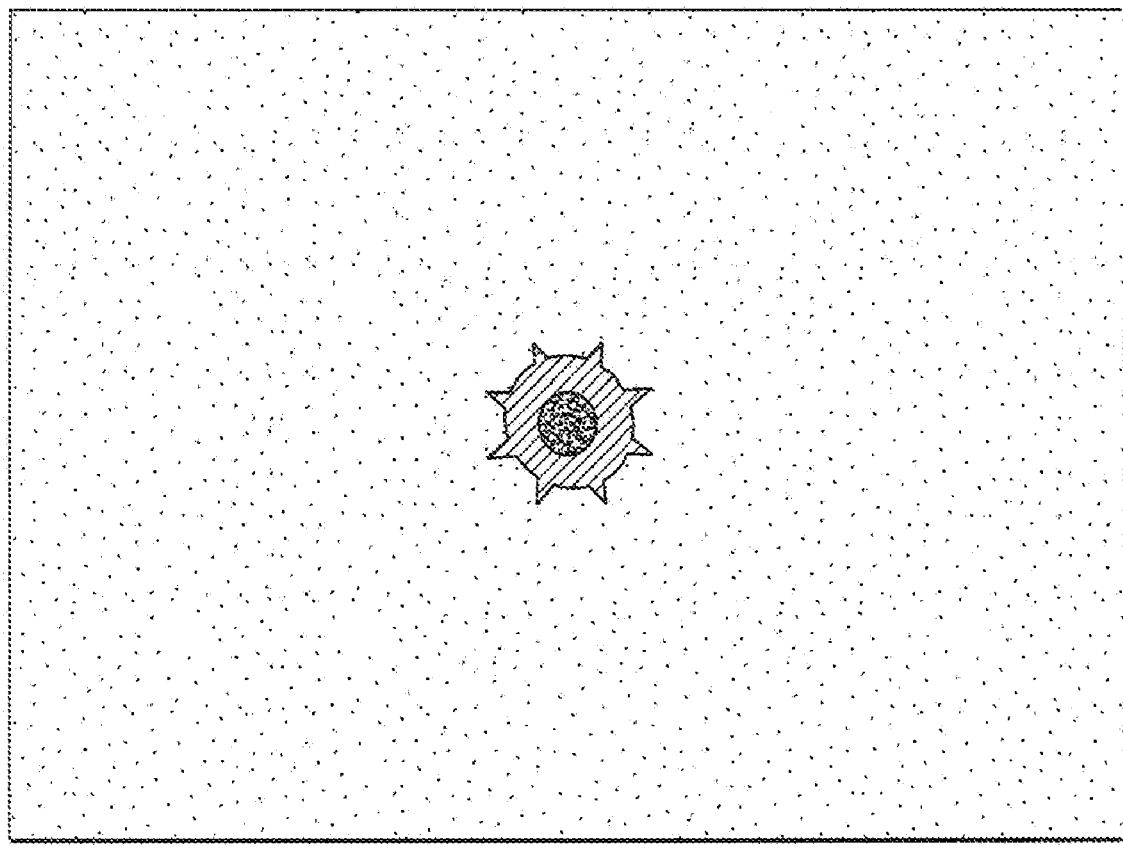
Figure 16:
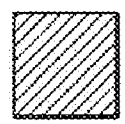
Figure 16:
Figure 16:
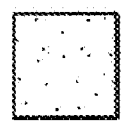
Figure 17:
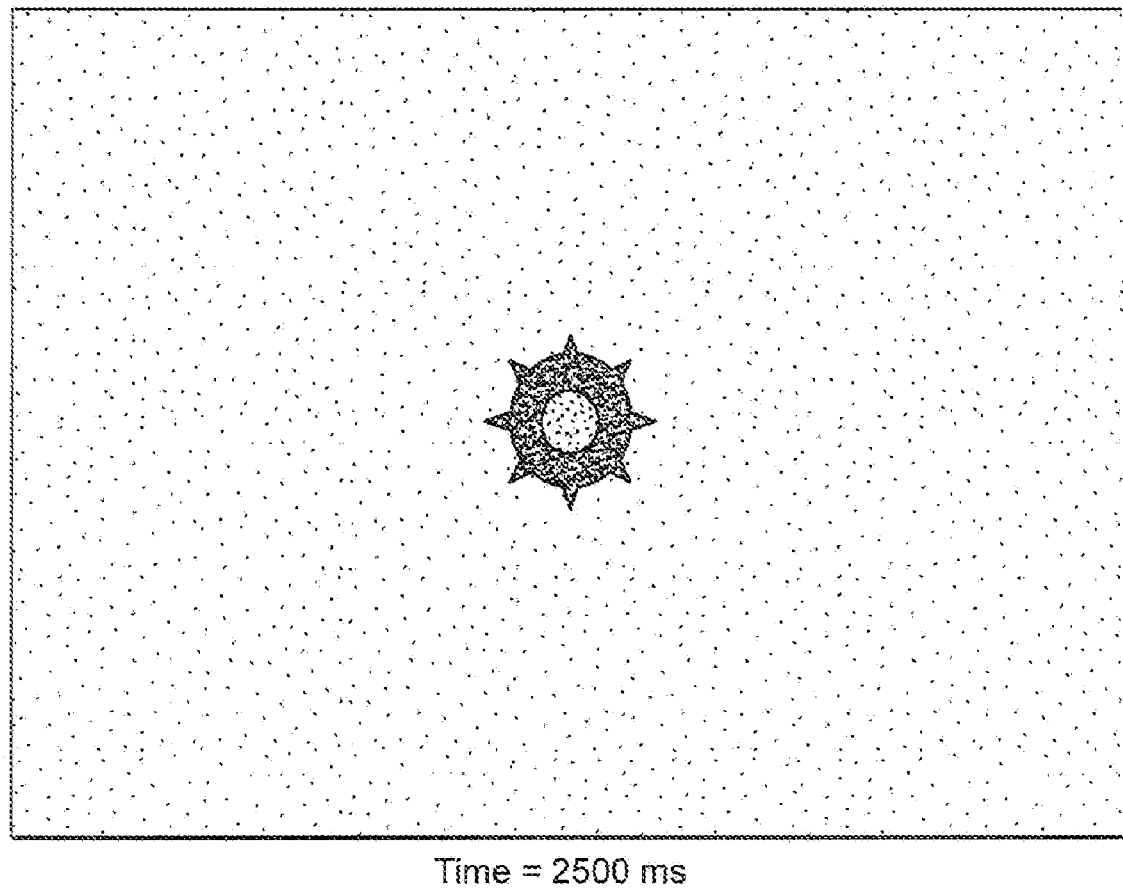
Figure 17:
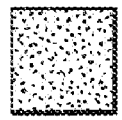
Figure 17:
Figure 17:

As shown in FIGS. 7 and 8, a fixation test cue 400 may be presented at various times. The subject may be instructed to respond to the appearance of the fixation test cue 400 via a computer input device. In this way, maintenance of visual fixation upon the stimulus 300 may be tracked and/or measured. As shown by way of example, the fixation test cue 400 is a change in color of the translating oval from green to yellow, but could be any change in visually detectable characteristics, including a change in shape or movement-pattern of the stimulus. Optionally, the fixation test cue may also be translated; FIG. 7 shows the fixation test cue in a left (base) position and FIG. 8 shows the fixation test cue in a right (alternate) position. In this way, the fixation test cue may remain visible for a longer period of time.

In accordance with an embodiment of the invention, the timing of the translational movement may be performed at a variety of regular, or irregular timings; by way of example, the timing is based on a regular cycle of 2 Hz. In other words, the stimulus 300 is translated about every 250 ms. The following table lists the position, time and color of the stimulus, and corresponding figures:

| Time (ms) | Translational Position | Color | Corresponding FIG. | Comment |
|---|---|---|---|---|
| 0 | Left | Green | 4 | Base stimulus |
| 250 | Right | Green | 5 | Altered stimulus |
| 500 | Left | Green | 6 | |
| 750 | Right | Green | Not shown | |
| 1000 | Left | Green | Not shown | |
| 1250 | Right | Green | Not shown | |
| 1500 | Left | Green | Not shown | |
| 1750 | Right | Green | Not shown | |
| 2000 | Left | Green | Not shown | |
| 2250 | Right | Green | Not shown | |
| 2500 | Left | Green | Not shown | |
| 2750 | Right | Green | Not shown | |
| 3000 | Left | Green | Not shown | |
| 3250 | Right | Green | Not shown | |
| 3500 | Left | Green | Not shown | |
| 3750 | Right | Green | Not shown | |
| 4000 | Left | Yellow | 7 | Fixation Test Cue |
| 4250 | Right | Yellow | 8 | Fixation Test Cue |
| 4500 | Left | Green | 9 | |
| 4750 | Right | Green | 10 | |

FIGS. 11-17 show, in time sequence, a rotating fixation stimulus 500, in accordance with another embodiment of the invention. A subject may visually fixate upon a spiked corona 510, which rotates around a central core 520. Although shown with eight regularly arranged spikes 530, the corona 510, may have a greater or fewer number of spikes 530. The spikes may be arranged in either a regular or irregular manner around the core 520. While a subject's vision may saturate with regard to the unchanging parts of the rotating stimulus 500, the alternating positions of the rotating spikes 530 will render at least the spikes 530 continuously visible. A rotating fixation stimulus 500 of altered color (orange corona 210 with a green core 220), may be used as a test cue 600, and is shown in a base configuration in FIG. 15 and in a rotated, altered, configuration in FIG. 16. The corona may rotate in regular or irregular increments; in FIGS. 11-17, each increment of rotation is about 28°. The following table summarizes the illustrative embodiment shown in FIGS. 11-17.

In a specific embodiment, the test cue stimulus 600 is closely matched to the fixation stimulus in terms of luminosity. By closely matching the luminance of the test cue 600 and a fixation stimulus 500, the patient's fixation may be more precisely ascertained, and consequently, the patient may be forced to fixate more precisely upon the stimulus 500. Experimental data show that isoluminous test cues are visible only within about 2 degrees of visual angle. Conversely, if the test cue 600 varied greatly in luminance from the fixation stimulus 500, then a patient could detect the fixation change at greater angles, e.g., 6°, 10°, or even 15° off the line of proper fixation. The luminance of the test cue 600 may vary from the luminance of the base stimulus 500 by a value that is 10%, 5% or less of the base pattern luminance. For example, a test cue stimulus 600 may cycle between colors that are distinguishable when substantially isoluminous; e.g., a yellow test cue stimulus stimulus 600 having a luminance of 200 millicandela per square meter and a green fixation stimulus 500 pattern of 190 millicandela per square meter.

| Time (ms) | Rotation Position | Core 520 Color | Corona 510 Color | Corresponding FIG. | Comment |
|---|---|---|---|---|---|
| 0 | Base | Green | Yellow | 11 | |
| 250 | Altered | Green | Yellow | 12 | |
| 500 | Base | Green | Yellow | 13 | |
| 760 | Altered | Green | Yellow | 14 | |
| 1000 | Base | Green | Yellow | Not shown | |
| 1250 | Altered | Green | Yellow | Not shown | |
| 1510 | Base | Green | Yellow | Not shown | |
| 1750 | Altered | Green | Yellow | Not shown | |
| 2000 | Base | Orange | Green | 15 | Fixation Cue |
| 2250 | Altered | Orange | Green | 16 | Fixation Cue |
| 2500 | Base | Green | Yellow | 17 | Return to Standard Fixation Stimulus |

Figure 18:
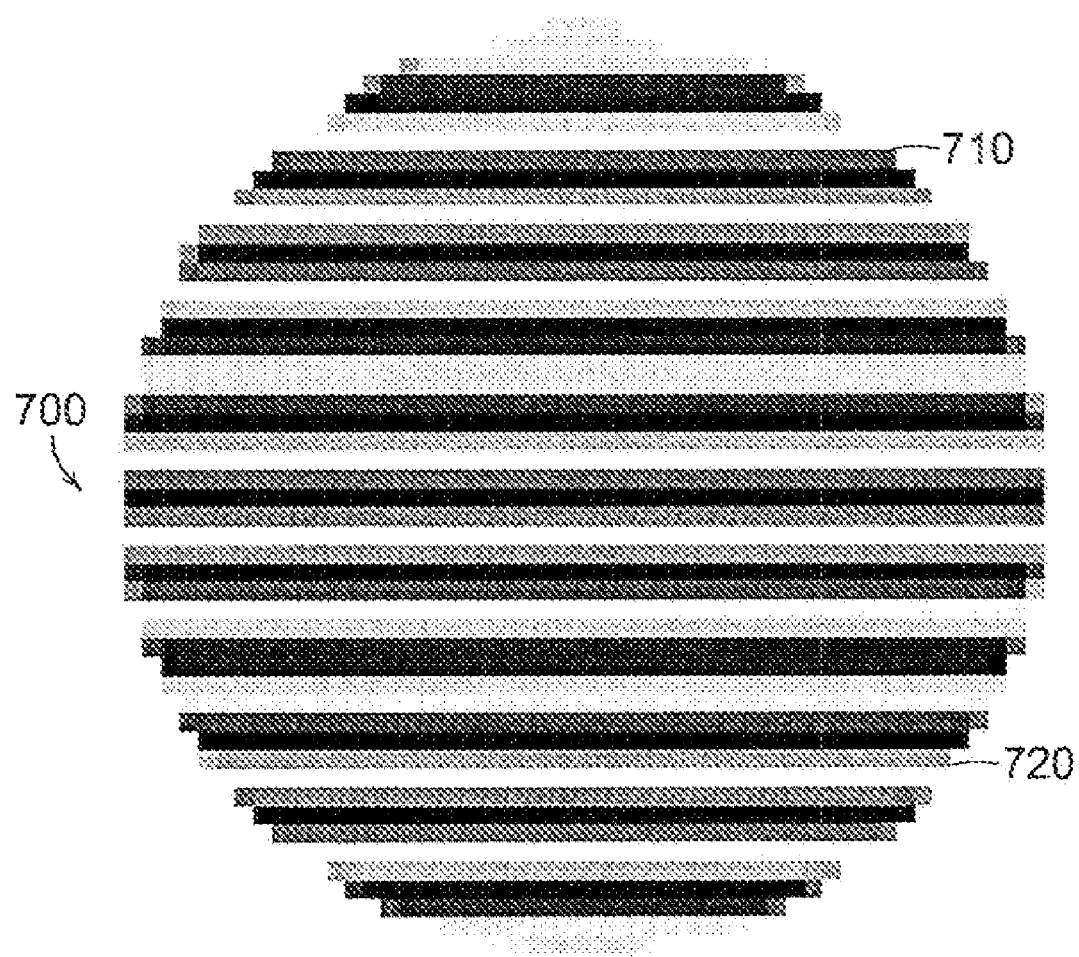
FIG. 18 shows a grating-like dynamic fixation stimulus in accordance with yet another embodiment of the invention, at a first time point.
Figure 19:
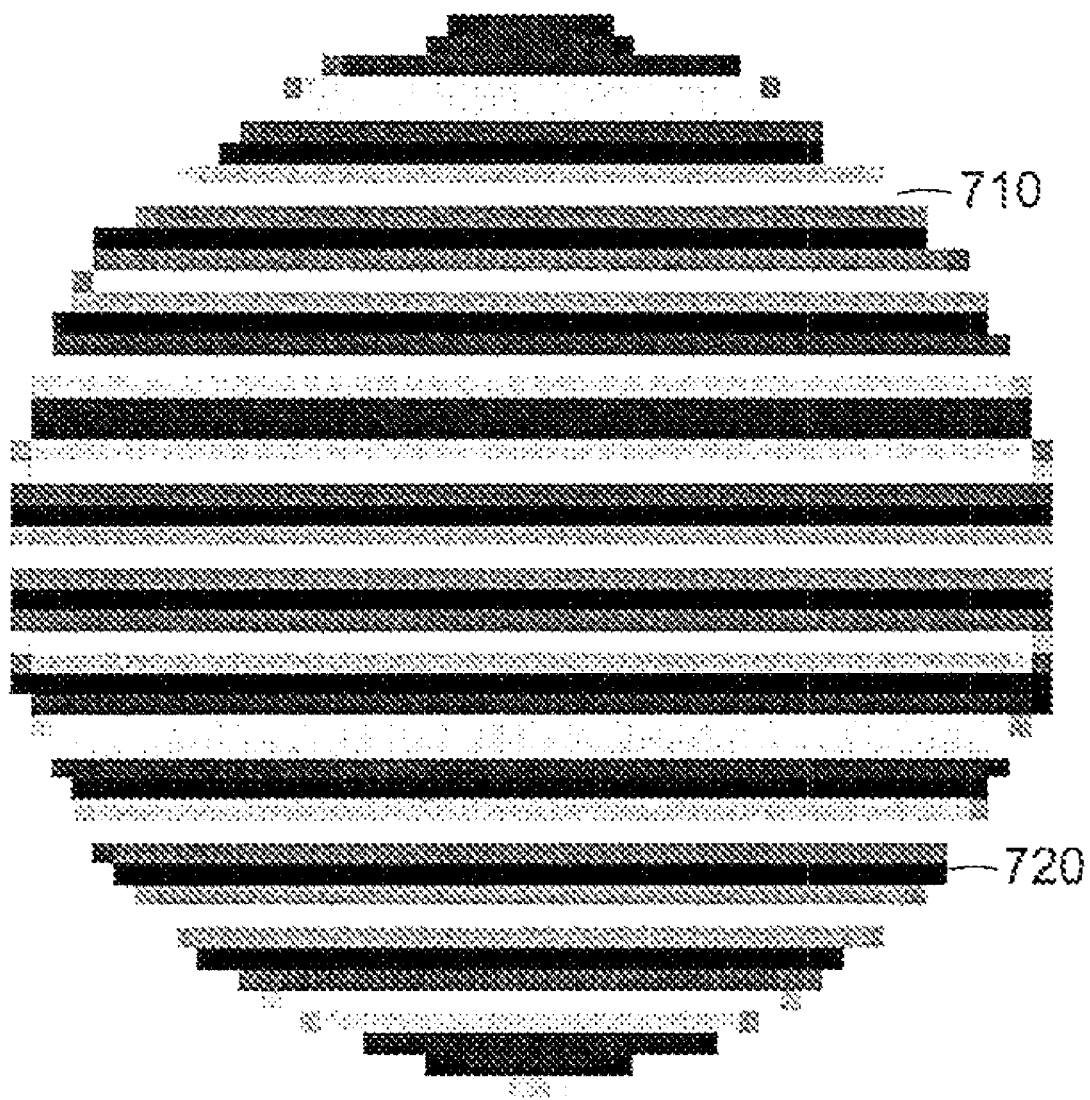
FIG. 19 shows a grating-like stimulus in accordance with the embodiment of FIG. 18 at a second time point.

FIGS. 18 and 19 show yet another embodiment in which a striated dynamic fixation stimulus 700 alternates with time between a positive (FIG. 18) and negative (FIG. 19) form. Low-luminosity areas 710 of the stimulus 700 in FIG. 18 have a high luminosity in FIG. 19. Conversely, high-luminosity areas 720 of the stimulus 700 in FIG. 18 have a low luminosity in FIG. 19. The stimulus 700 may repeatedly alternate between these positive and negative forms. If plotted versus time, the displayed luminosity of a given point or area within the stimulus 700 may vary in a square wave, sine wave (which would necessitate the use of intermediate shades of gray), or other repetitive pattern to allow alternate resensitization of saturated retinal regions. As in the preceding examples of FIGS. 4-17, the cycle frequency can vary, but may be optimal when above 0.5 Hz since retinal desensitization may occur after less than one second of stimulation. For example, the striations may alternate between bright and dark every 250 ms (2 Hz). The striations may also continuously or discontinuously rotate around a given point.

If the striations are sufficiently narrow in width, a subject should only be able to resolve the striations by using the central 1-2° of their visual field. As a result, loss of fixation will alter the striated appearance of the stimulus 700. Thus, the subject will be alerted very quickly if his or her fixation has wandered off target. Additionally, such high resolution features may be used with various embodiments of the invention as highly accurate test cues since such test cues should not be detectable using peripheral vision. Use of these test cues may result in increased accuracy in testing subject fixation, and may yield corresponding improvements in testing and training results.

Many variations of the stimulus 700 may be employed. For example, varying colors, patterns or other visually detectable properties may be used, including alternating between more than two such properties (e.g., changing points or regions from red to yellow, or green). While the use of sine waves and square waves described above implies alteration between two fixed levels, the levels may change with time in a pre-defined or semi-random manner.

In related embodiments of the present invention, dynamic stimuli like the dynamic fixation stimuli of FIGS. 1-18 may be used as peripheral spot stimuli for static or kinetic campimetry or perimetry, or as a component of visual restoration therapy (e.g., NovaVision VRT™; NovaVision, Inc, Boca Raton, Fla.).

In embodiments, a subject is tasked with fixating on a central fixation stimulus (static or dynamic) and responding to the appearance of a peripheral spot stimulus. The peripheral spot stimulus has a movement element to the presentation to cause preferential detection by the motion sensitive portion of the visual pathway (a "dynamic peripheral stimulus"). However, the peripheral spot stimulus is still a "spot" in the sense that is presented within bounds that define a fraction of the visual field comparable to the fraction of a visual field that might be stimulated by a static spot stimulus. Thus, the stimulus may be an animation within narrowly defined bounds, i.e., bounds that are substantially less than the visual field of the subject. For example, the bounds may correspond to 5%, 3%, or 1% or the patient's visual filed. The dynamic peripheral stimulus may be a single spot or coherent group of spots or objects. The stimulus may be adjustable in size, brightness, hue, frequency or other parameter. The dynamic peripheral stimulus may be used to map the visual field through perimetry or campimetry, to stimulate visual field region in a visual restoration therapy session, or both. Accordingly, user input may be collected to indicate perception of the dynamic peripheral spot stimuli.

Figure 20:
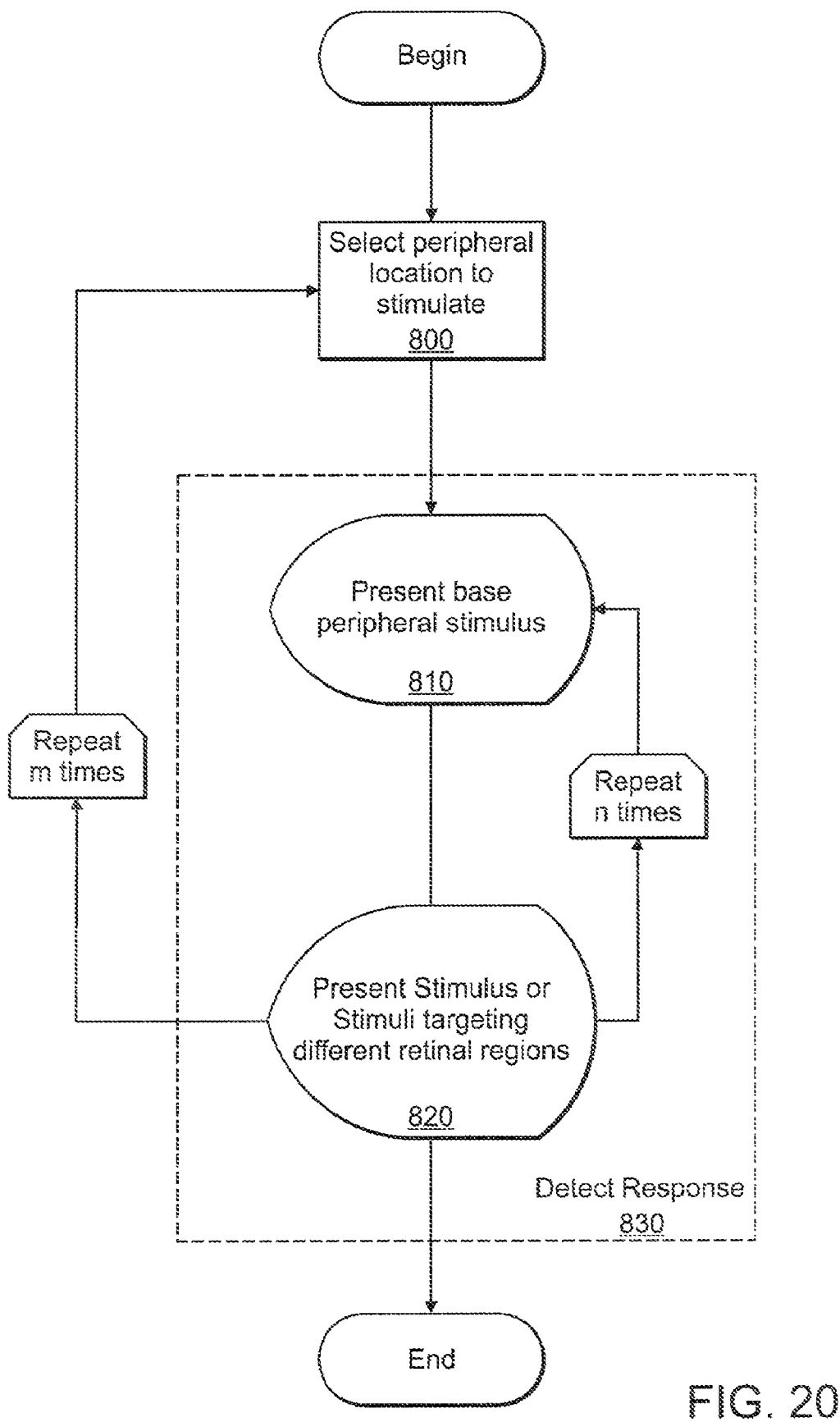
FIG. 20 is a flow chart of a method for creating a dynamic peripheral stimulus and recording a subject's response to the stimulus.

FIG. 20 is a flow diagram for a presentation of the dynamic peripheral spot stimulus. A peripheral location in which the dynamic peripheral spot stimulus is to be applied is selected (step 800). The location may be based on a previous perimetry or campimetry. For example, the border of the motion-sensitive visual field may be determined using kinetic perimetry. Motion sensitive visual-field regions on, near or within this border may then be tested or stimulated for therapeutic purposes using the dynamic peripheral spot stimulus. The overall size of the stimulus may occupy a relatively small fraction of the visual field to increase campimetry resolution or therapeutic specificity. For example, the boundary of the stimulus may consist of 10-20 pixels on a computerized display.

A base peripheral stimulus is presented at the selected location (step 810). Like the above-described fixation stimuli, the stimulus is then altered to target a different retinal region (step 820). The subject's motion-sensitive visual pathway may detect this alteration. Steps 810 and 820 may be repeated a given number of times while awaiting a response from the subject (step 830). Optionally, if there is no response from the subject an additional characteristic (e.g., luminosity, contrast, motion frequency, or hue) of the dynamic peripheral stimulus may be altered; when used for campimetry, a multidimensional motion-sensitive visual-field map may be thereby created. Upon receiving a response from the subject or reaching a time-out or other termination condition, a new location is chosen (step 800). This process (steps 800-830) is repeated until a visual-field map of sufficient detail is created, or until therapy is complete.

By stimulating visual-field regions that do not respond to static stimuli, dynamic peripheral stimuli may be useful for testing and treating subjects that have not optimally responded to other stimuli, and for use with patients having extremely poor vision (e.g., end stage glaucoma, optic atrophy, or retinitis pigmentosa). Dynamic peripheral stimulus may be incorporated as a feature into existing perimeters.

Example One

An isoluminous circular spot of small angular subtense (e.g. 11 pixels on an LCD monitor) is programmed to appear at pre-determined locations within the testing or therapy area of the applicable device. The circular spot of light "blinks" on and off at a pre-determined frequency but does not deviate from its original location.

Example Two

Two small (e.g. 5 pixels on an LCD screen), vertically elongated ellipses of light (paired side-by side) appear at a pre-determined location within the testing or therapy area and alternate illumination at a pre-determined frequency (e.g., right-left-right-left . . . ). The stimulus is modulated in appearance to trigger the percept of motion but the stimulus remains fixed in its location until detection or a pre-determined length of time.

Figure 22:
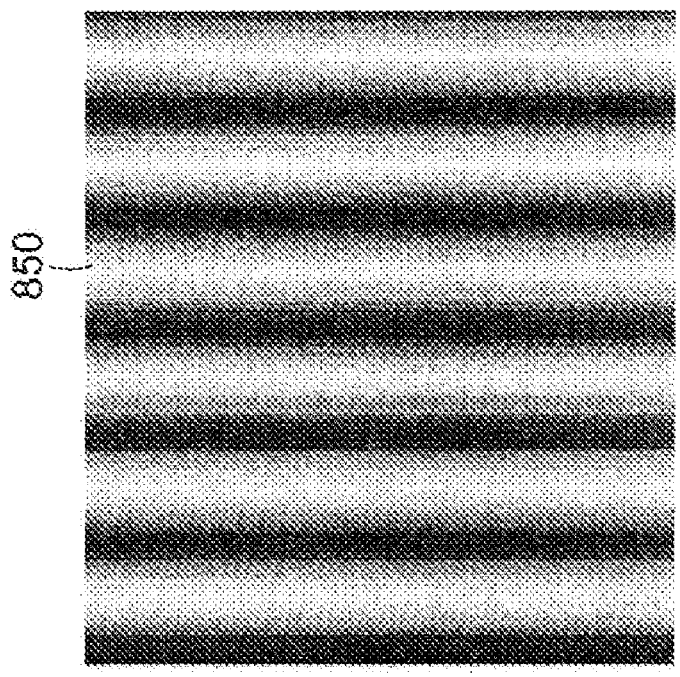
FIG. 22 shows the frequency doubling grating fixation stimulus of FIG. 21, as perceived by a subject.
Figure 21:
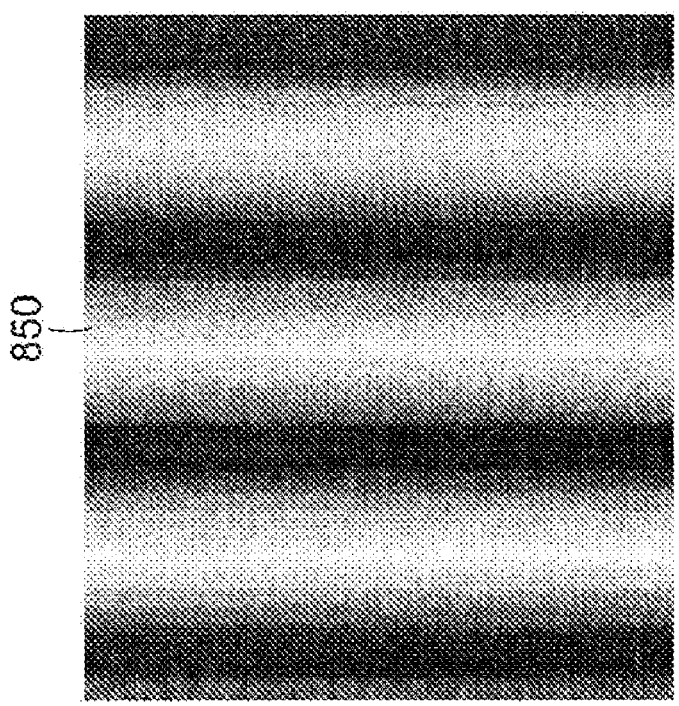
FIG. 21 shows a frequency doubling grating fixation stimulus as displayed on a computerized display.

In another embodiment of the invention, a frequency doubling grating may be used as a fixation stimulus in a way that creates an optical illusion. FIG. 21 shows a frequency doubling grating 850 as displayed upon a computer display in a brief moment of time. Like the frequency doubling gratings used for FDT, the spatial luminosity phase of the frequency doubling grating 850 is cycled above the critical flicker frequency, e.g., 25 Hz, to create a frequency doubling optical illusion. FIG. 22 shows how such an optical illusion might appear to a healthy subject. Unlike prior art gratings, however, the grating 850 of FIGS. 21-22 is used as a fixation stimulus, rather than a peripheral test stimulus. Peripheral stimuli used in connection with the grating 850 may be any of those described herein, among others. By appropriately tuning the frequency doubling grating 850, the frequency doubling optical illusion will only be visible to a subject if it illuminates the very central portion of the subject's retina. As a result, very small deviations in fixation will be noticeable to the subject and testable via an appropriate test cue (e.g., a change in the orientation, or other detectable change in the grating 850). For example, due to the structure of the human visual system, movement of the patient's fixation be as little as 2° will result in about a 50% decrease in spatial resolution. With an appropriately configured frequency doubling grating 850, the standard deviation in eye position over the course of therapy may be improved by a factor of about 1-2°. By increasing the mean accuracy of fixation in this manner, the precision and effectiveness of peripheral testing or stimulatory treatment may be improved. When such a dynamic stimulus is used in visual restoration therapy, a greater fraction of the peripheral stimuli may thereby be correctly allocated to appropriate visual field regions.

Figure 23:
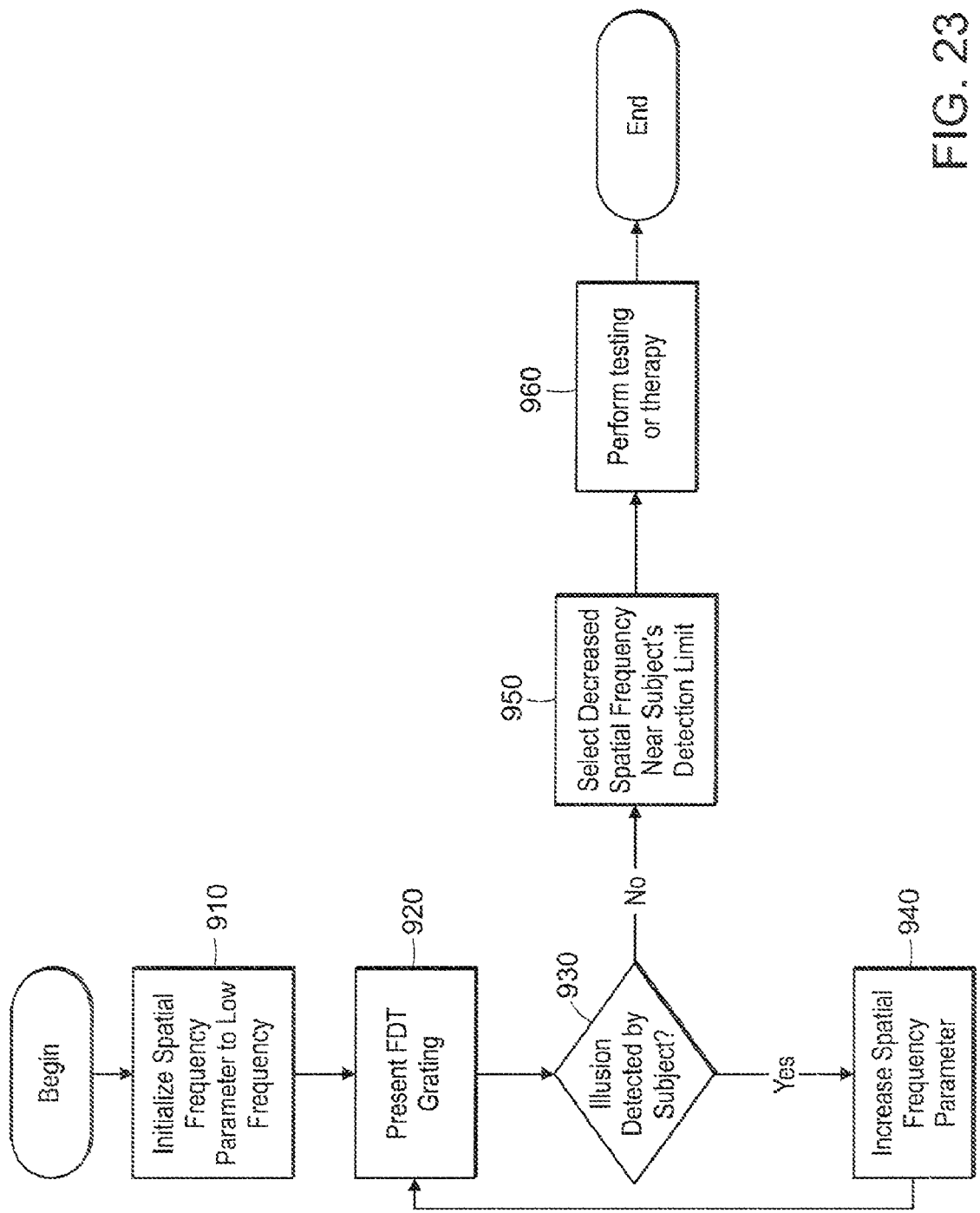
FIG. 23 is a flow chart for a method of tuning and using the frequency doubling grating fixation stimulus of FIGS. 21-22.

Due to disease, injury, genetic or other source of variation, different subjects vary in terms of their spatial resolution ability. Therefore, an individualized spatial frequency tuning may be beneficial before beginning testing or training. By tuning the spatial frequency of the grating 850, the subject will be forced to maintain a tighter fixation. FIG. 23 shows a flow chart for a tuning process in accordance with an embodiment of the invention. A spatial frequency parameter controls the spatial frequency of the grating 850 presented on a computerized display. This parameter is initialized to a low frequency starting point, e.g., one that can be detected as frequency doubling illusion by a majority, e.g. 90%, of patients or greater (step 910). The grating 850 is then presented as a frequency doubling fixation stimulus (step 920). If the subject detects the illusion (decision step 930), the spatial frequency parameter is increased and the higher frequency grating 850 is presented again at step 920. This process is repeated until a threshold frequency is reached at which the individual striations of the grating 850 are no longer detectable (decision step 930). The spatial frequency parameter is then decreased to one that is just below the threshold frequency. Accordingly, the spatial frequency adjusted stimulus is then detectable by the subject only with use of the most spatially sensitive region of the subject's visual field. For example, the frequency parameter may be set to be between 2% and 15% lower than the threshold frequency.

Since the grating 850 is presented at a high flicker rate, the subject's retina may be desensitized to the striations. To avoid desensitization, the grating 850 may be systematically perturbed to alternately stimulate different retinal regions; e.g., rotated or translated, as in the embodiments described with reference to FIGS. 1-19. The grating 850 may also be alternated with a fixation test cue, also described above.

In alternative embodiments, the disclosed methods for vision fixation, testing and training may be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared, laser or other transmission techniques). The series of computer instructions embodies all or part of the functionality previously described herein with respect to the system. Those skilled in the art should appreciate that such computer instructions can be written in a number of programming languages for use with many computer architectures or operating systems.

Furthermore, such instructions may be stored in any memory device, such as semiconductor, magnetic, optical or other memory devices, and may be transmitted using any communications technology, such as optical, infrared, microwave, laser or other transmission technologies. It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over the network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

The described embodiments of the invention are intended to be merely exemplary and numerous variations and modifications will be apparent to those skilled in the art. All such variations and modifications are intended to be within the scope of the present invention as defined in the appended claims.

What is claimed is:

1. A method for maintaining visual fixation for testing or treating the vision of a subject comprising:
   providing, for the subject to visually fixate upon, a fixation stimulus; and
   repeatedly altering the stimulus to create an optical illusion that is only detectable by use of the subject's central visual field; and
   while the subject is fixated upon the optical illusion, presenting a peripheral stimulus to the subject.

2. A method in accordance with claim 1, further comprising tuning the difficulty level of the optical illusion to match the spatial perception ability of the subject.

3. A method in accordance with claim 1, wherein the optical illusion is a frequency doubling illusion.

4. A method in accordance with claim 3, wherein the illusion comprises a frequency doubling grating.

5. A method in accordance with claim 4, wherein the tuning of the difficulty level includes varying the spatial frequency of the grating.

6. A method in accordance with claim 4, wherein the tuning includes increasing the spatial frequency of the grating until the illusion is not properly detected by the subject and then maintaining the spatial frequency at a level that is detectable by the subject, yet near the limit of the spatial resolution of the subject's central visual field.

7. A method according to claim 4, further comprising recording the patient's response to the peripheral stimulus.

\* \* \* \* \*